US012577179B2

(12) United States Patent
Farmer et al.

(10) Patent No.: US 12,577,179 B2
(45) Date of Patent: Mar. 17, 2026

(54) METHODS AND COMPOSITIONS FOR SOIL REGENERATION AND IMPROVED SOIL HYDROLOGY

(71) Applicant: Locus Solutions IPCo, LLC, Solon, OH (US)

(72) Inventors: Sean Farmer, Ft. Lauderdale, FL (US); Karthik N. Karathur, Solon, OH (US)

(73) Assignee: LOCUS SOLUTIONS IPCO, LLC, Solon, OH (US)

( * ) Notice: Subject to any disclaimer, the term of this patent is extended or adjusted under 35 U.S.C. 154(b) by 51 days.

(21) Appl. No.: 18/012,066

(22) PCT Filed: Oct. 14, 2022

(86) PCT No.: PCT/US2022/046679

§ 371 (c)(1),
(2) Date: Dec. 21, 2022

(87) PCT Pub. No.: WO2023/069313

PCT Pub. Date: Apr. 27, 2023

(65) Prior Publication Data

US 2024/0116831 A1 Apr. 11, 2024

Related U.S. Application Data

(60) Provisional application No. 63/256,688, filed on Oct. 18, 2021.

(51) Int. Cl.

| | |
|---|---|
| ***C05F 11/08*** | (2006.01) |
| ***C05G 3/50*** | (2020.01) |
| ***C09K 17/14*** | (2006.01) |
| *B82Y 5/00* | (2011.01) |

(52) U.S. Cl.

CPC ................ *C05F 11/08* (2013.01); *C05G 3/50* (2020.02); *C09K 17/14* (2013.01); *B82Y 5/00* (2013.01)

(58) Field of Classification Search

CPC ............ C09K 17/14; C05F 11/08; C05G 3/50
See application file for complete search history.

(56) References Cited

U.S. PATENT DOCUMENTS

| | | | | |
|---|---|---|---|---|
| 3,458,953 | A * | 8/1969 | Moses | C09K 17/14 47/58.1 R |
| 2005/0022570 | A1* | 2/2005 | Duarte-MacDonald | C05B 13/06 71/33 |
| 2007/0295670 | A1 | 12/2007 | Bassett | |
| 2010/0327071 | A1 | 12/2010 | Basset | |
| 2018/0272396 | A1 | 9/2018 | Farmer et al. | |

FOREIGN PATENT DOCUMENTS

| | | | | |
|---|---|---|---|---|
| CA | 2750644 | * | 8/2010 | C05D 9/00 |
| WO | 2017044953 | A1 | 3/2017 | |
| WO | WO-2018049182 | A2 * | 3/2018 | A61P 43/00 |
| WO | 2020219432 | A1 | 10/2020 | |
| WO | 2021030385 | A1 | 2/2021 | |
| WO | 2021183526 | A1 | 9/2021 | |

OTHER PUBLICATIONS

Aboud, H.M., et al., "Interaction of Bacillus Subtilis and Trichoderma Harzianum with Mycorrhiza on Growth and Yield of Cucumber (*Cucumis sativus* L.)." International Journal of Current Research, 2014 6(8): 7754-7758.
Alexis, Z. P., et al. "Effect of soil amendment with Trichoderma harzianum and Bacillus amyloliquefaciens bioformulation on biochemical parameters and antioxidant activity in Abelmoschus esculentus." International Journal of Innovation and Applied Studies, 2021, 33(3): 522-535.
Moore, D., et al. "The effect of soil surfactants on soil hydrological behavior, the plant growth environment, irrigation efficiency and water conservation." Journal of hydrology and hydromechanics, 2010, 58(3): 142-148.
Souza, K. S. T., et al. "Improvement of biosurfactant production by Wickerhamomyces anomalus CCMA 0358 and its potential application in bioremediation." Journal of hazardous materials, 2018, 346: 152-158.
Extended European Search Report issued in European Patent Application No. 22884290.2, dated Jun. 24, 2025.

* cited by examiner

*Primary Examiner* — Wayne A Langel
(74) *Attorney, Agent, or Firm* — Benesch Friedlander Coplan & Aronoff LLP

(57) ABSTRACT

The subject invention provides compositions and methods of their use for improving soil structure and hydrology. Advantageously, the compositions and methods of the subject invention can be formulated as environmentally-friendly, non-toxic and cost-effective solutions to the growing problems of, for example, water shortages, water-use inefficiency, declining soil health, nutrient leaching and runoff, and soil-borne greenhouse gas emissions.

14 Claims, No Drawings

METHODS AND COMPOSITIONS FOR SOIL REGENERATION AND IMPROVED SOIL HYDROLOGY

CROSS-REFERENCE TO RELATED APPLICATION

This application is a National Stage Application of International Application No. PCT/US2022/046679, filed Oct. 14, 2022; which claims priority to U.S. Provisional Patent Application No. 63/256,688, filed Oct. 18, 2021, both of which are incorporated herein by reference in their entirety.

BACKGROUND OF THE INVENTION

Soil is a complex mixture of minerals, gases, liquids, organic matter and microorganisms. The specific composition of a particular type of soil varies based on factors such as, for example, human activity, geographic location and climate.

Soil organic carbon (SOC) is an important component of soil matter and consists mainly of plant and animal tissue remains, live microbial biomass, and the by-products of microbial processes, as well as organo-mineral complexes. As part of the broader carbon exchange cycle, even minor changes in SOC can have a large impact on the levels of atmospheric carbon dioxide in a region (1 Pg of soil carbon stock=0.47 ppm of atmospheric CO2). Sequestration of SOC occurs when CO2 is transferred from the atmosphere into the soil by way of plant and microbe residues and other organic materials, which are stored in the soil with a long mean residence time (MRT). SOC sequestration can be achieved by, for example, increasing plant growth, retaining above and below-ground plant biomass, and/or protecting and stabilizing the SOC against erosion and decomposition.

Degradation, compaction, hydrophobicity and inefficient water and nutrient transport are all examples of problems that can arise in certain soils, each of which can lead to negative environmental impacts as well as negative outcomes for farmers. Thus, soil regeneration has become an important part of soil management for ecologists and farmers alike. Soil regeneration involves the rejuvenation of soil health by minimizing the degradation and erosion of topsoil, retaining more SOC than is depleted, increasing soil biodiversity, and maintaining proper water and nutrient cycling.

The degradation of soil is a growing problem, particularly for high organic content soils such as muck soils. Certain types of soils can degrade over time (sometimes referred to as "subsidence") as a result of draining, which leads to oxygenation of the soil environment and speeds up the aerobic breakdown of organic matter by soil microorganisms and/or their extracellular enzymes. Furthermore, dry surface soil can be eroded by wind.

Additionally, as the amount of microbial decomposition of carbon-rich organic matter in soil increases, the result is an increase in the rate of atmospheric greenhouse gas (GHG) emissions, such as carbon dioxide, methane and nitrous oxide, from these processes and a decrease in the amount of SOC.

A positive soil carbon budget is created by increasing the input of biomass carbon to exceed the SOC losses by erosion and decomposition. The rate of decomposition of biomass is affected by many factors, including, for example, climate, moisture levels, and types of plant matter—live or dead—present in the soils (Lal 2018).

An additional important factor impacting the rate of soil carbon accumulation is soil aggregate formation and stability. Healthy and robust root systems are effective for forming and stabilizing carbon-capturing soil aggregates, where organic matter and minerals become enmeshed in the roots. Soil microorganisms (e.g., fungal hyphae), and the growth by-products thereof (e.g., polysaccharides), can also facilitate association of carbon with soil mineral particles to form and stabilize these aggregates. Furthermore, studies have shown that the greater the soil aggregate size, the lower the degradation of soil by extracellular enzymes produced by microorganisms that consume organic matter in soil (Trivedi, P. et al. 2017; Trivedi, P. et al. 2015; Possinger et al. 2020; Grandy 2007).

Particle size distribution, organic matter content, mineralogy and water content can also be causes of soil compaction, where soil particles become pressed together, thereby reducing the pore space in between. Well-sorted, fine sandy loamy and loamy fine sands with a high fine sand fraction and low carbon content are particularly susceptible to compaction.

Compaction can also be caused by, for example, livestock trampling, use of heavy machinery, certain irrigation practices, and poorly managed tilling practices. While no-till practices are thought to improve SOC buildup via increased soil aggregation, no-till or reduced-till practices may actually increase soil compaction in the first few years of their employment. It can take several years before the build-up of SOC and growth of soil microaggregates from reduced tilling begin to counteract the negative effects of soil compaction that are brought about as a result.

Over time, compaction leads to physical soil degradation, reduced microbial populations, reduced SOC, modification of the size, structure and number of pores. In turn, soil strength increases, along with bulk density, while conductivity, permeability and diffusivity of water and air are reduced. Soil layers with high penetration resistance decrease rooting depth and density, which lead to a reduction in plant nutrient uptake, water uptake and water-use efficiency. Furthermore, inefficient water and nutrient transport can cause runoff of phosphates and nitrates, leading to, for example, harmful algal blooms.

Soil hydrophobicity is another problem that can occur in soils. Soils can be naturally hydrophobic in nature, and this is often exacerbated when the soil is left to dry for an extended time or has a high organic content. Fires can also induce or intensify soil water repellency as hydrophobic substances in the soil and litter are volatilized, pyrolyzed, and redistributed deeper into the soil profile.

The hydrophobic nature of soil can limit the penetration and infiltration of irrigation-based applications. Soil hydrophobicity can lead to water pooling, evaporation and surface run-off, which has a direct consequence on plant growth through restriction of water infiltration and supply to root zone of plants.

One further issue that can have drastic effects on both the agriculture and livestock industries is water usage. In certain areas of the country, over farming, over-industrialization and/or over-development are leading to a reduction in ground water and aquifer levels. In other areas, droughts occur, leading to widespread water shortages and reduced crop yields. The amount of water required to irrigate large tracts of farm land, as well as the amount of water needed for drinking by livestock animals, necessitates increased water use efficiency for both industries, where less water is required to achieve a desired production level.

Soil surfactants (or wetting agents) have been utilized to counteract the deleterious effects of soil water repellence and poor water-use efficiency. The mode of action varies among commercial products, but in general, surfactants are composed of organic molecules with hydrophobic tails and hydrophilic heads. This chemical structure allows for lowering of the the surface tension of the water, thus increasing infiltration of water between soil particles. Furthermore, surfactants render the soil wettable, as the hydrophobic tail of the wetting agent chemically bonds to the hydrophobic coating on the soil particle, while the hydrophilic head attracts water molecules and transports them into the soil. While soil surfactants can be effective tools for managing water usage and soil health, many of these compounds are synthetic chemicals that can persist in the environment. Some might even be toxic to humans and/or animals.

The economic costs and environmental impacts of current methods of producing crops and caring for lawns and gardens continue to burden the sustainability of the agriculture and horticulture industries. Soil health and water and nutrient use efficiency are important aspects that factor into this burden. Accordingly, there is a need for improved, safe approaches to addressing soil and water management for farmers, landscapers, and every day consumers.

BRIEF SUMMARY OF THE INVENTION

The subject invention provides compositions and methods of their use for improving irrigation of soil. Advantageously, the compositions and methods of the subject invention can be formulated as environmentally-friendly, non-toxic and cost-effective solutions to the growing problems of, for example, water shortages, water-use inefficiency, declining soil health, nutrient leaching and runoff, and soil-borne greenhouse gas emissions.

In certain embodiments, the compositions and methods of the subject invention can be useful for any of the following exemplary benefits:

a) improving the dispersion, percolation and/or retention of water and nutrients throughout the layers of soil, thereby improving water and nutrient uptake by plant roots and reducing water and fertilizer usage requirements;
b) improving the circulation of water and nutrients within plant vasculature, even in colder climates;
c) decreasing and/or preventing soil compaction, thereby improving water, nutrient, root and microbial movement throughout the soil;
d) reducing the pooling of water on and in soil, thereby reducing evaporation, runoff and waterlogging; and
e) increasing soil organic content (SOC) and reducing soil-borne greenhouse gas emissions.

In certain embodiments, the subject invention provides irrigation additives comprising a surface-active molecule. The surface-active molecule can be a synthetic surfactant, a microbial- or plant-derived biosurfactant, and/or a surfactant produced using naturally-derived substrates. In preferred embodiments, the surface-active molecule serves as a wetting agent, which, when contacted with water in soil, enhances the watering efficiency for plants, including crops, turf and ornamentals.

In preferred embodiments, the surface-active agent of the subject composition has a micelle size less than 100 nm, less than 75 nm, less than 50 nm, and more preferably less than 25 nm. In certain embodiments, the micelle size is less than 10 nm, less than 8 nm, or less than 5 nm.

In preferred embodiments, the surface-active molecule is a microbial-derived biosurfactant. The biosurfactant can be applied in purified and/or crude form. Crude form biosurfactants can comprise, for example, biosurfactants and other products of cellular growth, including fermentation medium resulting from cultivation of a biosurfactant-producing microbe.

Biosurfactants according to the subject methods can be selected from, for example, low molecular weight glycolipids (e.g., sophorolipids, cellobiose lipids, rhamnolipids, mannosylerythritol lipids and trehalose lipids), lipopeptides (e.g., surfactin, iturin, fengycin, arthrofactin and lichenysin), flavolipids, phospholipids (e.g., cardiolipins), fatty acid esters, and high molecular weight polymers such as lipoproteins, lipopolysaccharide-protein complexes, and polysaccharide-protein-fatty acid complexes.

In certain specific embodiments, the biosurfactant is a sophorolipid (SLP), such as, for example, a lactonic SLP, an acidic SLP, an amino acid-SLP conjugate, a salt-form SLP, or a derivative of any of these.

In certain embodiments, the irrigation additive can comprise additional substances, such as, for example, carriers, pH adjusters, pesticides, herbicides, fertilizers, microbial inoculants, mineral sources, plant seeds, dyes, stabilizers, emulsifiers, prebiotics and/or polymers.

In certain embodiments, the subject invention provides methods of irrigating a soil, the methods comprising combining an amount of an irrigation additive according to the subject invention with an aqueous fluid to create a treated irrigation fluid, and administering the treated irrigation fluid to the soil. In certain embodiments, the irrigation additive is applied with the aqueous fluid continuously throughout irrigation. Advantageously, the subject methods improve soil health, soil hydrology, and, consequently, lead to improved plant health.

In some embodiments, the method comprises applying the irrigation additive to soil in a dry form or mixed with a carrier without first mixing the irrigation additive with an aqueous fluid, wherein untreated irrigation water and/or rainwater activate the irrigation additive upon contact therewith in, or on, the soil. Thus, in some embodiments, the method comprises applying the irrigation additive to soil, followed by applying an aqueous irrigation fluid to the soil.

In certain embodiments, the irrigation additive is applied to a soil to reduce the surface and/or interfacial tension between the water and soil particles, thereby providing one or more of: improved dispersion, penetration and/or percolation of water and nutrients into the soil during irrigation; loosening of hard or compacted soils; and increased soil porosity and aeration. Advantageously, this can increase the space for root growth, air movement, and water holding capacity within the soil.

In certain embodiments, the irrigation additive is particularly helpful for reducing surface and/or interfacial tension between water and soil, as well as increasing porosity of compacted soils, due to its nanoparticle micelle size. The ultra-small micelle size of the irrigation additive allows water to penetrate into micro- and nano-sized pores in hard and tightly packed soils, thereby loosening the pores and allowing for increased air, nutrient and water flow. This can further help prevent root rot caused by excessive water, which can cause overgrowth of detrimental fungi in the soil and on roots.

In certain embodiments, the irrigation additive lowers the surface and/or interfacial tension between water and root cells, thereby facilitating enhanced transport of water and nutrients into, and throughout, plant vascular systems.

Advantageously, the method can reduce the water usage requirements for achieving a desired level of irrigation by at least 15%, at least 20%, at least 25%, or at least 30% compared with irrigating without the irrigation additive.

Advantageously, in certain embodiments, the irrigation additive is effective in a wide range of temperatures. Accordingly, in some embodiments, application of the irrigation additive to soil in colder locations and climates (e.g., locations further away from the equator, locations at high altitudes, and temperate locations during winter months) can promote circulation thereof despite plant dormancy, reduced cell metabolism and/or reduced water transport efficiency due to the lower temperature. Furthermore, in some embodiments, application of the irrigation additive to soil in warmer climates (e.g., locations nearer to the equator, locations in desert regions, and temperate locations during summer months) can be particularly useful for reducing water pooling and evaporation due to high temperatures.

The methods are effective for improving irrigation of soil in a wide variety of conditions, including, for example, compacted soil, arid soil, eroded soil, nutrient-depleted soil, water-logged soil, fire-damaged soil, hydrophobic soil, and/or soil with plants growing therein.

In certain embodiments, the subject methods can be further enhanced with the application of one or more microbial soil treatment compositions. For example, in certain embodiments, the irrigation additive is applied to soil first, followed by application of the microbial soil treatment composition after a period of time (e.g., 30 days). This cycle can be repeated indefinitely and/or until a desired level of irrigation and/or a desired level of improvement in soil health, soil hydrology and/or plant health is achieved.

In certain embodiments, the soil treatment compositions comprise one or more soil-colonizing microorganisms and/or growth by-products thereof, such as biosurfactants, enzymes and/or other metabolites. The composition may also comprise the fermentation medium in which the microorganism(s) were produced.

In certain embodiments, the microorganisms are bacteria, yeasts and/or fungi. In some embodiments, the composition comprises more than one type and/or species of microorganism.

In one embodiment, the soil treatment composition comprises a *Bacillus* sp. bacterium, such as, e.g., *B. amyloliquefaciens* NRRL 13-67928 or *B. subtilis* NRRL B-68031. In one embodiment, the composition comprises a *Trichoderma* sp. fungus, such as, e.g., *T. harzianum* T-22. In certain embodiments, the *Bacillus* sp. and the *Trichoderma* sp. are utilized together.

In one embodiment, the composition comprises one or more yeasts, such as, for example, *Wickerhamomyces anomalus, Meyerozyma guilliermondii, Meyerozyma caribbica* (e.g., *M. caribbica* MEC14XN, a.k.a. *M. caribbica* subsp. Locus.) *Saccharomyces boulardii, Debaryomyces hansenii, Pichia occidentalis* and/or *Pichia kudriavzevii.*

Advantageously, in some embodiments, the microorganisms colonize the soil and convert root exudates and digested organic matter into bulky, carbon-rich microbial biomass and necromass (dead cells). In some embodiments, the microorganisms form biofilms. In some embodiments, the one or more microbes colonize plant roots, and aid in, for example, solubilizing nutrients for plant root uptake, dispersing water and salts throughout the rhizosphere, and/or increasing above and below-ground plant biomass, compared with untreated soils and/or plants.

In certain embodiments, the subject methods can be useful for reducing compaction while enhancing SOC sequestration via, for example, increased above- and below-ground plant biomass, increased microbial biomass and/or necromass, and/or increased size and/or stability of soil aggregates. Furthermore, in some embodiments, the subject methods can be utilized in combination with no-till or reduced-till practices to reduce soil compaction that results from these practices.

Additionally, in certain embodiments, the subject methods can reduce the soil-borne emission of greenhouse gases, such as carbon dioxide, methane and nitrous oxide, which are caused by, for example, over-use and/or low bioavailability of fertilizers, and/or the decomposition of soil by low carbon use efficiency (CUE) microbes.

The methods and compositions of the subject invention can be used either alone or in combination with other compositions and methods for efficiently enhancing soil and/or plant health. For example, in some embodiments, the method comprises applying additional components, such as herbicides, fertilizers, pesticides and/or other soil amendments, to the soil and/or plants. The exact materials and the quantities thereof can be determined by, for example, a grower or soil scientist having the benefit of the subject disclosure.

Advantageously, the subject compositions and methods can help regenerate soil resources that are traditionally considered non-renewable, while improving water-use efficiency, suppressing and/or averting soil GHG emissions and reducing the need for synthetic fertilizers.

DETAILED DESCRIPTION OF THE INVENTION

The subject invention provides compositions and methods of their use for improving soil irrigation. Advantageously, the compositions and methods of the subject invention can be formulated as environmentally-friendly, non-toxic and cost-effective solutions to the growing problems of, for example, water shortages, water-use inefficiency, declining soil health, nutrient leaching and runoff, and soil-borne greenhouse gas emissions.

Selected Definitions

As used herein, "agriculture" means the cultivation and breeding of plants for food, fiber, biofuel, medicines, cosmetics, supplements, ornamental purposes and other uses. According to the subject invention, agriculture can also include horticulture, landscaping, gardening, plant conservation, forestry and reforestation, pasture and prairie restoration, orcharding, arboriculture, and agronomy. Further included in agriculture are the care, monitoring and maintenance of soil.

As used herein, a "broth," "culture broth," or "fermentation broth" refers to a culture medium comprising at least nutrients and microorganism cells.

As used herein, the term "carbon use efficiency" or "CUE" refers to a generalized measure of the efficiency by which microbes allocate carbon taken up towards growth and biomass production versus respiration. CUE can be calculated as growth (biomass production) over the sum of $CO_2$ production/emissions and growth. Microorganisms are often categorized as "low CUE" or "high CUE," where a CUE greater than 0.50 is considered high, and a CUE lower than 0.50 is considered low.

Unless the context requires otherwise, the phrases "fermenting," "fermentation process" or "fermentation reaction" and the like, as used herein, are intended to encompass both the growth phase and product biosynthesis phase of the process.

As used herein, an "isolated" or "purified" compound is substantially free of other compounds, such as cellular material, with which it is associated in nature. A purified or isolated polynucleotide (ribonucleic acid (RNA) or deoxyribonucleic acid (DNA)) is free of the genes or sequences that flank it in its naturally-occurring state. A purified or isolated polypeptide is free of the amino acids or sequences that flank it in its naturally-occurring state. "Isolated" in the context of a microbial strain means that the strain is removed from the environment in which it exists in nature. Thus, the isolated strain may exist as, for example, a biologically pure culture, or as spores (or other forms of the strain) in association with a carrier.

As used herein, a "biologically pure culture" is a culture that has been isolated from materials with which it is associated in nature. In a preferred embodiment, the culture has been isolated from all other living cells. In further preferred embodiments, the biologically pure culture has advantageous characteristics compared to a culture of the same microbe as it exists in nature. The advantageous characteristics can be, for example, enhanced production of one or more growth by-products.

In certain embodiments, purified compounds are at least 60% by weight the compound of interest. Preferably, the preparation is at least 75%, more preferably at least 90%, and most preferably at least 99%, by weight the compound of interest. For example, a purified compound is one that is at least 85%, 90%, 91%, 92%, 93%, 94%, 95%, 98%, 99%, or 100% (w/w) of the desired compound by weight. Purity is measured by any appropriate standard method, for example, by column chromatography, thin layer chromatography, or high-performance liquid chromatography (HPLC) analysis.

As used herein, "enhancing" means improving or increasing. For example, enhanced plant health means improving the plant's ability grow and thrive, which includes increased seed germination and/or emergence, improved immunity against pests and/or diseases, and improved ability to survive environmental stressors, such as droughts and/or overwatering. Enhanced plant growth and/or enhanced plant biomass means increasing the size and/or mass of a plant above and/or below the ground (e.g., increased canopy/foliar volume, height, trunk caliper, branch length, shoot length, protein content, root size/density and/or overall growth index), and/or improving the ability of the plant to reach a desired size and/or mass. Enhanced yields mean improving the end products produced by the plants in a crop, for example, by increasing the number and/or size of fruits, leaves, roots and/or tubers per plant, and/or improving the quality of the fruits, leaves, roots and/or tubers (e.g., improving taste, texture, brix, chlorophyll content and/or color).

A "metabolite" refers to any substance produced by metabolism (e.g., a growth by-product) or a substance necessary for taking part in a particular metabolic process. A metabolite can be an organic compound that is a starting material, an intermediate in, or an end product of metabolism. Examples of metabolites include, but are not limited to, biosurfactants, biopolymers, enzymes, acids, solvents, alcohols, proteins, vitamins, minerals, microelements, and amino acids.

The subject invention utilizes "microbe-based compositions," meaning a composition that comprises components that were produced as the result of the growth of microorganisms or other cell cultures. Thus, the microbe-based composition may comprise the microbes themselves and/or by-products of microbial growth. The microbes may be in a vegetative state, in spore or conidia form, in hyphae form, in any other form of propagule, or a mixture of these. The microbes may be planktonic or in a biofilm form, or a mixture of both. The by-products of growth may be, for example, metabolites, cell membrane components, proteins, and/or other cellular components. The microbes may be intact or lysed. In preferred embodiments, the microbes are present, with growth medium in which they were grown, in the microbe-based composition. The microbes may be present at, for example, a concentration of at least $1\times10^4$, $1\times10^5$, $1\times10^6$, $1\times10^7$, $1\times10^8$, $1\times10^9$, $1\times10^{10}$, $1\times10^{11}$, $1\times10^{12}$ or $1\times10^{13}$ or more CFU per gram or per ml of the composition.

The subject invention further provides "microbe-based products," which are products that are to be applied in practice to achieve a desired result. The microbe-based product can be simply a microbe-based composition harvested from a microbe cultivation process. Alternatively, the microbe-based product may comprise further ingredients that have been added. These additional ingredients can include, for example, stabilizers, buffers, appropriate carriers, such as water, salt solutions, or any other appropriate carrier, added nutrients to support further microbial growth, non-nutrient growth enhancers and/or agents that facilitate tracking of the microbes and/or the composition in the environment to which it is applied. The microbe-based product may also comprise mixtures of microbe-based compositions. The microbe-based product may also comprise one or more components of a microbe-based composition that have been processed in some way such as, but not limited to, filtering, centrifugation, lysing, drying, purification and the like.

As used herein, the term "plant" includes, but is not limited to, any species of woody, ornamental or decorative, crop or cereal, fruit plant or vegetable plant, flower or tree, macroalga or microalga, phytoplankton and photosynthetic algae (e.g., green algae *Chlamydomonas reinhardtii*). "Plant" also includes a unicellular plant (e.g., microalga) and a plurality of plant cells that are largely differentiated into a colony (e.g., volvox) or a structure that is present at any stage of a plant's development. Such structures include, but are not limited to, a fruit, a seed, a shoot, a stem, a leaf, a root, a flower petal, etc. Plants can be standing alone, for example, in a garden, or can be one of many plants, for example, as part of an orchard, crop or pasture.

As used herein, "crop plants" refer to any species of plant or alga, grown for profit and/or for sustenance for humans, animals or aquatic organisms, or used by humans (e.g., textile, cosmetics, and/or drug production), or viewed by humans for pleasure (e.g., flowers or shrubs in landscaping or gardens) or any plant or alga, or a part thereof, used in industry, commerce or education. Crop plants can be plants that can be obtained by traditional breeding and optimization methods or by biotechnological and recombinant methods, or combinations of these methods, including the transgenic plants and the plant varieties.

All plants and plant parts can benefit from the subject invention. In this context, plants are understood as meaning all plants and plant populations such as desired and undesired wild plants or crop plants (including naturally occurring crop plants).

Plant tissue and/or plant parts are understood as meaning all aerial and subterranean parts and organs of the plants such as shoots, leaves, flowers, roots, needles, stalks, stems, fruits, seeds, tubers and rhizomes. The plant parts also include crop material and vegetative and generative propagation material, for example cuttings, tubers, rhizomes, slips and seeds.

As used herein "preventing" or "prevention" of a situation or occurrence means delaying, inhibiting, suppressing, forestalling, and/or minimizing the onset, extensiveness or progression of the situation or occurrence. Prevention can include, but does not require, indefinite, absolute or complete prevention, meaning it may still develop at a later time. Prevention can include reducing the severity of the onset of such a situation or occurrence, and/or stalling its development to a more severe or extensive situation or occurrence.

Ranges provided herein are understood to be shorthand for all of the values within the range. For example, a range of 1 to 20 is understood to include any number, combination of numbers, or sub-range from the group consisting of 1, 2, 3, 4, 5, 6, 7, 8, 9, 10, 11, 12, 13, 14, 15, 16, 17, 18, 19, 20, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 50 may comprise 1 to 10, 1 to 20, 1 to 30, and 1 to 40 in one direction, or 50 to 40, 50 to 30, 50 to 20, and 50 to 10 in the other direction.

As used herein, "reduction" refers to a negative alteration, and the term "increase" refers to a positive alteration, wherein the negative or positive alteration is at least 0.25%, 0.5%, 1%, 5%, 10%, 15%, 20%, 25%, 30%, 35%, 40%, 45%, 50%, 55%, 60%, 70%, 75%, 80%, 85%, 90%, 95%, or 100%.

As used herein, "reference" refers to a standard or control condition.

As used herein, a "soil amendment" or a "soil conditioner" is any compound, material, or combination of compounds or materials that are added into soil to enhance the properties of the soil and/or rhizosphere. Soil amendments can include organic and inorganic matter, and can further include, for example, fertilizers, pesticides and/or herbicides. Nutrient-rich, well-draining soil is essential for the growth and health of plants, and thus, soil amendments can be used for enhancing the plant biomass by altering the nutrient and moisture content of soil. Soil amendments can also be used for improving many different qualities of soil, including but not limited to, soil structure (e.g., preventing compaction); improving the nutrient concentration and storage capabilities; improving water retention in dry soils; and improving drainage in waterlogged soils.

As used herein, "surfactant" refers to a compound that lowers the surface tension (or interfacial tension) between phases. Surfactants act as, e.g., detergents, wetting agents, emulsifiers, foaming agents, and dispersants. A "biosurfactant" is a surfactant produced by a living organism.

The transitional term "comprising," which is synonymous with "including," or "containing," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention. Use of the term "comprising" contemplates other embodiments that "consist" or "consist essentially" of the recited component(s).

Unless specifically stated or obvious from context, as used herein, the term "or" is understood to be inclusive. Unless specifically stated or obvious from context, as used herein, the terms "a," "and" and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof. All references cited herein are hereby incorporated by reference in their entirety.

Methods for Irrigating Soils

The subject invention provides compositions and methods of their use for improving the health, structure and hydrology of soil. Advantageously, the compositions and methods of the subject invention can be formulated as environmentally-friendly, non-toxic and cost-effective solutions to the growing problems of, for example, water shortages, water-use inefficiency, declining soil health, nutrient leaching and runoff, and soil-borne greenhouse gas emissions.

In certain embodiments, the compositions and methods of the subject invention can be useful for any of the following exemplary benefits:

a) improving the dispersion, percolation and retention of water and nutrients throughout the layers of soil, thereby improving water and nutrient uptake by plant roots and reducing water and fertilizer usage requirements;
b) improving the circulation of water and nutrients within plant vasculature, even in colder climates;
c) decreasing and/or preventing soil compaction, thereby improving water, nutrient, air, root and microbial movement throughout the soil;
d) reducing the pooling of water on and in soil, thereby reducing evaporation, runoff and waterlogging; and
e) increasing soil organic content (SOC) and reducing soil-borne greenhouse gas emissions.

The subject invention provides irrigation additive compositions, as well as methods irrigation a soil, wherein the methods comprise applying the irrigation additive to the soil. Advantageously, the subject compositions and methods improve soil health, soil hydrology, and, consequently, plant health.

In certain embodiments, the irrigation additive according to the subject invention is a soil amendment or soil conditioner.

In certain embodiments, the irrigation additive comprises a surface-active molecule. The surface-active molecule can be a synthetic surfactant, a microbial- or plant-derived biosurfactant, and/or a surfactant produced using naturally-derived substrates. In preferred embodiments, the surface-active molecule serves as a wetting agent, which, when contacted with water in soil, enhances the watering efficiency for plants, including crops, turf and ornamentals.

In preferred embodiments, the surface-active molecule is a microbial-derived biosurfactant. The biosurfactant can be applied in purified and/or crude form. Crude form biosurfactants can comprise, for example, biosurfactants and other products of cellular growth in the leftover fermentation medium resulting from cultivation of a biosurfactant-producing microbe.

Biosurfactants according to the subject methods can be selected from, for example, low molecular weight glycolipids (e.g., sophorolipids, cellobiose lipids, rhamnolipids, mannosylerythritol lipids and trehalose lipids), lipopeptides (e.g., surfactin, iturin, fengycin, arthrofactin and lichenysin), flavolipids, phospholipids (e.g., cardiolipins), fatty acid esters, and high molecular weight polymers such as lipoproteins, lipopolysaccharide-protein complexes, and polysaccharide-protein-fatty acid complexes.

In certain specific embodiments, the biosurfactant is a sophorolipid (SLP), such as, for example, a lactonic SLP, an acidic SLP, a salt-form SLP, or a derivative of any of these.

As used herein, the term "sophorolipid," "sophorolipid molecule," "SLP" or "SLP molecule" includes all forms, and isomers thereof, of SLP molecules, including, for example, acidic (linear) SLP (ASL) and lactonic SLP (LSL). Further included are mono-acetylated SLP, di-acetylated SLP, esterified SLP, SLP with varying hydrophobic chain lengths, cationic and/or anionic SLP with fatty acid-amino acid complexes attached, esterified SLP, SLP-metal complexes, SLP-salt derivatives (e.g., a sodium salt of a linear SLP), SLP amino alcohols, SLP with carbonyl groups removed from the aliphatic chain, and other, including those that are and/or are not described within in this disclosure.

In preferred embodiments, the SLP according to the subject invention are represented by General Formula (1) and/or General Formula (2), and are obtained as a collection of multiple structural homologues:

(1)

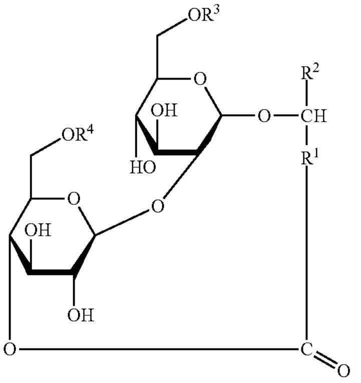

(2)

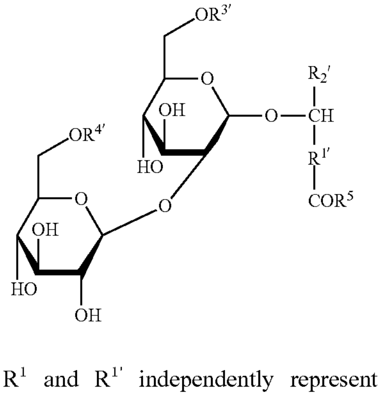

where $R^1$ and $R^{1'}$ independently represent saturated hydrocarbon chains or single or multiple, in particular single, unsaturated hydrocarbon chains having 8 to 20, in particular 12 to 18 carbon atoms, more preferably 14 to 18 carbon atoms, which can be linear or branched and can comprise one or more hydroxy groups, $R^2$ and $R^{2'}$ independently represent a hydrogen atom or a saturated alkyl functional group or a single or multiple, in particular single, unsaturated alkyl functional group having 1 to 9 carbon atoms, more preferably 1 to 4 carbon atoms, which can be linear or branched and can comprise one or more hydroxy groups, and $R^3$, $R^{3'}$, $R^4$ and $R^{4'}$ independently represent a hydrogen atom or $-COCH_3$. $R^5$ is typically an H.

SLP are typically produced by yeasts, such as *Starmerella* spp. yeasts and/or *Candida* spp. yeasts, e.g., *Starmerella* (*Candida*) *bombicola, Candida apicola, Candida batistae, Candida floricola, Candida riodocensis, Candida stellate* and/or *Candida kuoi*. In a specific embodiment, the microorganism is *Starmerella bombicola*, e.g., strain ATCC 22214. SLP have environmental compatibility, high biodegradability, low toxicity, high selectivity and specific activity in a broad range of temperature, pH and salinity conditions.

In some embodiments, the surface-active molecule is another type of surfactant, including synthetic and/or commercially available surfactants. These can include, for example, TWEEN 20, TWEEN 40, TWEEN 60, TWEEN 80, TWEEN 21, SPAN, INCROCAS 30, INCROCAS 35, INCROCAS 40, ACCONON C-10, ACCONON CA-15, ACCONON CA-9, ACCONON CC-6, CROVAL A-40, CROVAL A-70, GELUCIRE 44/14, GELUCIRE 50/13, LABRASOL, SOLUTOL HS 15, VOLPO 10, VOLPO 20, PLURONIC F108, PLURONIC F127, PLURONIC F68, PLURONIC F87, PLURONIC L44, PLURONIC R 17R4, TETRONIC 304, OP-10, Calfoam ES-603, Nonidet P40, Triton X-100, TERGITOL 15-S-9, polyoxyl 40 stearate, polyoxyl 50 stearate, triblock co-polymers of ethylene oxide/propylene oxide/ethylene oxide, sorbitan monopalmitate, sorbitan monostearate, glycerol monostearate, polyoxyethylene stearate, polyoxyethylene 40 sorbitol lanolin derivative, polyoxyethylene 75 sorbitol lanolin derivative, polyoxyethylene 6 sorbitol beeswax derivative, polyoxyethylene 20 sorbitol beeswax derivative, polyoxyethylene 20 sorbitol lanolin derivative, polyoxyethylene 50 sorbitol lanolin derivative, polyoxyethylene 23 lauryl ether, polyoxyethylene 23 lauryl ether, polyoxyethylene 2 cetyl ether, polyoxyethylene 10 cetyl ether, polyoxyethylene 20 cetyl ether, polyoxyethylene 2 stearyl ether, polyoxyethylene 10 stearyl ether, polyoxyethylene 20 stearyl ether, polyoxyethylene 21 stearyl ether, polyoxyethylene 20 oleyl ether, polyoxyethylene 40 stearate, polyoxyethylene 50 stearate, polyoxyethylene 100 stearate, sorbitan monolaurate, sorbitan sesquialeate, sorbitan trioleate, polyoxyethylene sorbitan monolaurate, polyoxyethylene sorbitan monostearate, sorbitan monopalmitate, sorbitan monostearate, sorbitan tristearate, polyoxyethylene 4 sorbitan monostearate, polyoxyethylene 20 sorbitan tristearate, sodium lauryl sulfate, sodium dodecyl sulfate, ammonium lauryl sulfate, alkyl phenol ethoxylates (e.g., octylphenoxy polyethoxyethanol), spolyethylene glycol monooleate, polyethylene glycol alkylate, polyoxyethylene alkyl ether, polyglycol diether, lauroyl diethanolamide, fatty acid iso-propanolamide, maltitol hydroxy fatty acid ether, alkylated polysaccharide, alkyl glucoside, sugar ester, oleophillic, glycerol monostearate, self-emulsifiable glycerol monostearate, polyglycerol monostearate, polyglycerol alkylate, sorbitan monooleate, polyethylene glycol monostearate, polyoxyethylene sorbitan monooleate, polyoxyethylene cetyl ether, polyoxyethylene sterol, polyoxyethylene lanolin, polyoxyethylene bees wax, and polyoxyethylene hydrogenated castor oil, alcohol ethoxylates, linear primary alcohol ethoxylates, primary aliphatic oxyalkylated alcohols, nonyl phenol ethoxylate, primary alkyl poly(oxyethylene ether), alkyl polyglycosides, poly(ethylene oxide-co-propylene oxide), stearyl dimethylbenzyl ammonium chloride, stearyl trimethyl ammonium chloride, benzalkonium chloride, and laurylamine oxide, alkylaminoethyl glycine chloride, lecithin, sodium stearate, potassium palmitate, sodium cetyl sulfate, sodium lauryl phosphate, sodium polyoxyethylene lauryl sulfate, triethanolamine palmitate, polyoxyethylene sodium lauryl phosphate, and sodium N-acyl glutamate or combinations thereof.

In certain preferred embodiments, the surface-active agent is not a lauryl sulfate.

In preferred embodiments, the surface-active agent of the subject composition has a micelle size less than 100 nm, less than 75 nm, less than 50 nm, and more preferably less than 25 nm. In certain embodiments, the micelle size is less than 10 nm, less than 8 nm, or less than 5 nm.

For example, some commercial and/or synthetic surfactants have micelle sizes less than 20 nm, including Triton X-100 (7.5 nm), Tween-20 (8.5 nm), Tween-80 (11.7 nm), Nonidet P40 (15.4 nm), and sodium dodecyl sulfate (3.5-6 nm). Additionally, in some embodiments, the micelle size of a sophorolipid biosurfactant is less than 10 nm.

In certain embodiments, the irrigation additive having small micelle size (e.g., less than 20 nm) or, more preferably, an ultra-small micelle size (e.g., less than 10 nm), is particularly helpful for reducing surface and/or interfacial tension between water and soil, as well as increasing porosity of compacted soils. The micelle size of the irrigation additive allows water to penetrate into micro- and nano-sized pores in the tightly packed soil, thereby loosening the pores and allowing for increased root movement, microbial movement, and air, nutrient and water flow.

In certain embodiments, the irrigation additive can comprise additional substances, such as, for example, carriers, pH adjusters, pesticides, herbicides, fertilizers, microbial inoculants, mineral sources, soil amendments, soil conditioners, plant seeds, dyes, stabilizers, emulsifiers, prebiotics, and/or polymers.

In certain embodiments, the subject invention provides methods of irrigating a soil, the methods comprising combining an amount of an irrigation additive according to the subject invention with an aqueous fluid to create a treated irrigation fluid, and applying the treated irrigation fluid to the soil. In certain embodiments, the irrigation additive is applied continuously throughout irrigation of the soil.

In some embodiments, the method comprises applying the irrigation additive to soil in a dry form or mixed with a carrier without first mixing the irrigation additive with an aqueous fluid, wherein untreated irrigation water and/or rainwater activate the irrigation additive upon contact therewith in the soil. In such embodiments, the methods comprise applying irrigation fluids to the soil before or after the irrigation additive is administered to the soil, for example, within 24 hours, preferably within 12 hours, more preferably within 60 minutes before or after.

The aqueous irrigation fluid can include any available source of water, or treated water that has been combined with any additive taught herein for enhancing the performance of the treated irrigation water. The water can be from any common water source, such as rivers, lakes, and groundwater, and can include, for example, any potable water, some non-potable waters, and recycled water, such as the water from run-off.

In certain embodiments, the surface-active agent is utilized at a concentration, compared with the total amount of irrigation liquid being applied, of about 0.001% to about 50%, from about 0.01% to about 25%, from about 0.5% to about 15%, from about 2% to about 12%, from about 3% to about 10%, or any range therein, by weight.

In certain embodiments, the surface-active agent is utilized at a concentration, compared with the amount of water in the irrigation liquid, at a concentration of about 1 to 1,000 ppm, about 5 to 500 ppm, or about 10 to about 100 ppm.

In certain embodiments, the irrigation additive is applied to a soil to reduce the surface and/or interfacial tension between the water and soil contents, thereby providing improved dispersion, penetration and/or percolation of water and nutrients into the soil during irrigation; and reduced pooling of water on and in soil, thereby reducing evaporation, runoff and waterlogging.

In certain embodiments, the irrigation additive is applied to a soil to loosen hard or compacted soils via penetration of tight soil pores, resulting in increased soil porosity and aeration. Advantageously, this can increase the space for root growth and water holding capacity within the soil.

Advantageously, the method can reduce the water usage requirements for achieving a desired level of irrigation by at least 15%, at least 20%, at least 25%, or at least 30% compared with irrigating without the irrigation additive.

In some embodiments, the irrigation additive lowers the surface and/or interfacial tension between water and root cells, thereby facilitating enhanced transport of water and nutrients into, and throughout, plant vascular systems.

Advantageously, in certain embodiments, the irrigation additive is effective in a wide range of temperatures. Accordingly, in some embodiments, application of the irrigation additive to soil in colder locations and climates (e.g., locations further away from the equator, locations at high altitudes, and temperate locations during winter months) can promote circulation thereof despite dormancy, reduced metabolism and/or reduced water transport efficiency due to the lower temperature. Furthermore, in some embodiments, application of the irrigation additive to soil in warmer climates (e.g., locations nearer to the equator, locations in desert regions, and temperate locations during summer months) can be particularly useful for reducing water pooling and evaporation due to the high temperature.

In certain embodiments, the methods are effective for improving irrigation of a variety of soil conditions, including, for example, compacted soil, arid soil, eroded soil, nutrient-depleted soil, water-logged soil, fire-damaged soil, hydrophobic soil, and/or soil with plants growing therein.

In certain embodiments, the subject methods can be further enhanced with the application of one or more microbial soil treatment compositions. For example, in certain embodiments, the irrigation additive is applied to soil first, followed by application of the microbial soil treatment composition after a period of time (e.g., 20 to 60 days, or about 30 (+/−10) days). In certain embodiments, the microbial soil treatment is applied first, followed by the irrigation additive after a period of time (e.g., 20 to 60 days, or about 30 (+/−10) days). The cycle of either of these alternating applications can be repeated indefinitely and/or until a desired level of irrigation and/or a desired level of improvement in soil health, soil hydrology and/or plant health is achieved.

In certain embodiments, the microbial soil treatment compositions comprise one or more soil-colonizing microorganisms and/or growth by-products thereof, such as biosurfactants, enzymes and/or other metabolites. The composition may also comprise the fermentation medium in which the microorganism(s) were produced.

In certain embodiments, the microorganisms are bacteria, yeasts and/or fungi. In some embodiments, the composition comprises more than one type and/or species of microorganism.

In one embodiment, the soil treatment composition comprises a *Bacillus* sp. bacterium, such as, e.g., *B. amyloliq-*

*uefaciens* NRRL B-67928 or *B. subtilis* NRRL B-68031. In one embodiment, the composition comprises a *Trichoderma* sp. fungus, such as, e.g., *T. harzianum* T-22. In certain embodiments, the *Bacillus* sp. and the *Trichoderma* sp. are utilized together.

In one embodiment, the composition comprises one or more yeasts, such as, for example, *Wickerhamomyces anomalus, Meyerozyma guilliermondii, Meyerozyma caribbica* (e.g., *M. caribbica* MEC14XN, a.k.a. *M. caribbica* subsp. Locus), *Saccharomyces boulardii, Debaryomyces hansenii, Pichia occidentalis* and/or *Pichia kudriavzevii*. Other microorganisms, such as those described below, are also envisioned.

Advantageously, in some embodiments, the microorganisms colonize the soil and convert root exudates and digested organic matter into bulky, carbon-rich microbial biomass and necromass (dead cells). In some embodiments, the microorganisms form biofilms. In some embodiments, the one or more microbes colonize plant roots, and aid in, for example, solubilizing nutrients for plant root uptake, dispersing water and salts throughout the rhizosphere, and/or increasing above and below-ground plant biomass, compared with untreated soils and/or plants.

In certain embodiments, the subject methods can be useful for reducing compaction while enhancing SOC sequestration via, for example, increased above- and below-ground plant biomass, increased microbial biomass and/or necromass, and/or increased size and/or stability of soil aggregates. Furthermore, in some embodiments, the subject methods can be utilized in combination with no-till or reduced-till practices aimed at promoting soil aggregation and build-up of SOC, in order to reduce any soil compaction that results from these practices.

In some embodiments, the subject methods increase the above- and below-ground biomass of plants, which includes, for example, increased foliage volume, increased stem and/or trunk diameter, enhanced root growth and/or density, and/or increased total numbers of plants. In one embodiment, this is achieved by improving the overall hospitability of the rhizosphere in which a plant's roots are growing, for example, by improving the porosity of soil, the nutrient and/or moisture retention properties of the rhizosphere. In one embodiment, the soil treatment compositions enhance penetration of water and beneficial molecules through the outer layers of root cells, for example, at the root-soil interface of the rhizosphere.

In some embodiments, the methods can lead to improved biodiversity of the soil microbiome. As used herein, improving the biodiversity refers to increasing the variety of microbial species within the soil. In some embodiments, improved biodiversity comprises increasing the ratio of high CUE microorganisms to low CUE microorganisms, and/or converting low CUE microorganisms into high CUE microorganisms.

In some embodiments, the methods can lead to reduced instances of root rot caused by soggy, poor-draining soil. Roots are prevented from absorbing sufficient oxygen, causing oxygen starvation and root decay. The water-logged soil conditions also create an environment that facilitates increased sporulation and thriving of detrimental fungi that can include, for example, *Armillaria mellea, Clitocybe tabescens, Fusarium* spp., *Pythium* spp., *Phytophthora* spp., and *Aphanomyces* spp.

Additionally, in certain embodiments, the subject methods can reduce the soil-borne emission of greenhouse gases, such as carbon dioxide, methane and nitrous oxide, which are caused by, for example, over-use and/or low bioavailability of fertilizers, and/or the decomposition of soil by low carbon use efficiency (CUE) microbes.

In some embodiments, prior to applying a composition to the site, the method comprises assessing the site for local conditions, determining a preferred formulation for the composition (e.g., the type, combination and/or ratios of irrigation additives and/or microbial soil treatment compositions) that is customized for the local conditions, and producing the composition with the preferred formulation.

The local conditions can include, for example, soil conditions (e.g., soil type, level of compaction, species of soil microbiota, amount and/or type of soil organic content, amount and/or type of GHG precursor substrates, amount and/or type of fertilizers or other soil additives or amendments present); crop and/or plant conditions (e.g., types, numbers, age and/or health of plants being grown); environmental conditions (e.g., current climate, season, or time of year); amount and type of GHG emissions at the site; mode and/or rate of application of the composition, and others as are relevant to the site.

After assessment, a preferred formulation for the composition can be determined so that the composition can be customized for these local conditions. The composition is then cultivated, preferably at a microbe growth facility that is within 300 miles of the site of application, preferably within 200 miles, even more preferably within 100 miles.

In some embodiments the local conditions are assessed periodically, for example, once annually, biannually, or even monthly. In this way, the composition formula can be modified in real time as necessary to meet the unique needs of the changing local conditions.

In some embodiments, the subject methods also comprise performing one or more measurements to assess the effect of the methods of the subject invention on increasing soil moisture retention and dispersion, reducing compaction, the generation and/or reduction in generation of GHGs, and/or the accumulation of carbon in soil. In one embodiment, the method comprises simply sampling soil and testing moisture and composition.

In certain embodiments, the subject methods also comprise performing one or more measurements to assess the effect of the methods of the subject invention on the generation and/or reduction in generation of GHGs and/or on the accumulation of SOC in plants and/or soil.

Measurements can be conducted at a certain time point after application of the soil treatment composition to the site. In some embodiments, the measurements are conducted after about 1 week or less, 2 weeks or less, 3 weeks or less, 4 weeks or less, 30 days or less, 60 days or less, 90 days or less, 120 days or less, 180 days or less, and/or 1 year or less.

Furthermore, the measurements can be repeated over time. In some embodiments, the measurements are repeated daily, weekly, monthly, bi-monthly, semi-monthly, semi-annually, and/or annually.

In certain embodiments, assessing GHG generation can take the form of measuring GHG emissions from a site. Gas chromatography with electron capture detection is commonly used for testing samples in a lab setting. In certain embodiments, GHG emissions can also be conducted in the field, using, for example, flux measurements and/or in situ soil probing. Flux measurements analyze the emission of gases from the soil surface to the atmosphere, for example, using chambers that enclose an area of soil and then estimate flux by observing the accumulation of gases inside the chamber over a period of time. Probes can be used to generate a soil gas profile, starting with a measurement of the concentration of the gases of interest at a certain depth in the soil, and comparing it directly between probes and ambient surface conditions (Brummell and Siciliano 2011, at 118).

Measuring GHG emissions can also comprise other forms of direct emissions measurement, gas chromatography-mass spectrometry (GC-MS) and/or analysis of fuel input. Direct emissions measurements can comprise, for example, identifying polluting operational activities (e.g., fuel-burning automobiles) and measuring the emissions of those activities directly through Continuous Emissions Monitoring Systems (CEMS). Fuel input analysis can comprise calculating the quantity of energy resources used (e.g., amount of electricity, fuel, wood, biomass, etc., consumed) determining the content of, for example, carbon, in the fuel source, and applying that carbon content to the quantity of the fuel consumed to determine the amount of emissions.

In certain embodiments, carbon content of a site where plants are growing, e.g., agricultural site, crop, sod or turf farm, pasture/prairie or forest, can be measured by, for example, quantifying the aboveground and/or below-ground biomass of plants. In general, the carbon concentration of, for example, a tree, is assumed to be from about 40 to 50% of the biomass.

Biomass quantification can take the form of, for example, harvesting plants in a sample area and measuring the weight of the different parts of the plant before and after drying. Biomass quantification can also be carried out using non-destructive, observational methods, such as measuring, e.g., trunk diameter, height, volume, and other physical parameters of the plant. Remote quantification can also be used, such as, for example, laser profiling and/or drone analysis.

In some embodiments, carbon content of a site can further comprise sampling and measuring carbon content of litter, woody debris and/or soil of a sampling area. Soil, in particular, can be analyzed, for example, using dry combustion to determine percent total organic carbon (TOC); by potassium permanganate oxidation analysis for detecting active carbon; and by bulk density measurements (weight per unit volume) for converting from percent carbon to tons/acre.

In some embodiments, the subject invention can be used for reducing the number of carbon credits used by an operator involved in, e.g., agriculture, livestock production, forestry/reforestation, and wetland management.

The methods and compositions of the subject invention can be used either alone or in combination with other compounds for efficiently enhancing soil and/or plant health. For example, in some embodiments, the method comprises applying additional components, such as herbicides, fertilizers, pesticides and/or other soil amendments, to the soil and/or plants. The exact materials and the quantities thereof can be determined by, for example, a grower or soil scientist having the benefit of the subject disclosure.

In some embodiments, the methods are used in combination with existing soil regeneration practices, such as, for example, no-till or low-till farming, crop rotation, and/or the planting of off-season cover crops.

Modes of Application

As used herein, "applying" a composition or product to a site refers to contacting a composition or product with a site such that the composition or product can have an effect on that site. The mode of application depends upon the formulation of the composition, and can include, for example, spraying, pouring, sprinkling, injecting, spreading, mixing, dunking, fogging and misting. Formulations for the irrigation additive and/or the microbial soil treatment composition can include, for example, liquids, dry and/or wettable powders, flowable powders, dusts, granules, pellets, emulsions, microcapsules, steaks, oils, gels, pastes and/or aerosols.

In one embodiment, the site to which a composition of the subject invention is applied is soil (or rhizosphere), including soil in which plants will be planted or are growing (e.g., a crop, a field, an orchard, a grove, a pasture/prairie or a forest). The composition(s) of the subject invention can be pre-mixed with irrigation fluids, and/or the composition(s) can be applied to soil surfaces, with or without water, where the beneficial effect of the soil application can be activated by rainfall, sprinkler, flood, drip or other forms of irrigation.

In one embodiment, the site is a plant or plant part. The composition(s) can be applied directly thereto as a seed treatment, or to the surface of a plant or plant part (e.g., to the surface of the roots, tubers, stems, flowers, leaves, fruit, or flowers). In one embodiment, the composition(s) can be contacted with one or more roots of the plant. The composition(s) can be applied directly to the roots, e.g., by spraying or dunking the roots prior to planting, and/or indirectly, e.g., by administering the composition(s) to the soil in which the plant grows. The composition(s) can be applied to the seeds of the plant prior to or at the time of planting, or to any other part of the plant and/or its surrounding environment.

In one embodiment, wherein the method is used in a field, citrus grove, a pasture or prairie, a forest, a sod or turf farm, lawn, or another agricultural crop, the method can comprise administering the composition(s) into an irrigation system used for supplying water, fertilizers, pesticides or other liquid compositions. Thus, the plant and/or soil can be treated with the composition via, for example, soil injection, soil drenching, using a center pivot irrigation system, with a spray over the seed furrow, with micro-jets, with drench sprayers, with boom sprayers, with sprinklers and/or with drip irrigators. Advantageously, the method is suitable for treating hundreds or more acres of land.

In one embodiment, wherein the method is used in a smaller scale setting, the method can comprise pouring the composition(s) (mixed with water and other optional additives) into the tank of a handheld lawn and garden sprayer and spraying soil or another site with the composition. The composition(s) can also be mixed into a standard handheld watering can and poured onto a site.

Soil, plants and/or their environments can be treated at any point during the process of cultivating a plant. For example, the composition(s) can be applied to the soil prior to, concurrently with, or after the time when seeds or plants are planted therein. They can also be applied at any point thereafter during the development and growth of the plant, including when the plant is flowering, fruiting, and during and/or after abscission of leaves.

In one embodiment, the methods and compositions according to the subject invention lead to an increase in one or more of: root mass, stalk diameter, plant height, canopy density, chlorophyll content, flower count, bud count, bud size, bud density, leaf surface area, and/or nutrient uptake of a plant, by at least 1%, 5%, 10%, 20%, 30%, 40%, 50%, 60%, 70%, 80%, 90%, 100%, 150%, 200%, or more, compared to a plant growing in an untreated environment.

In one embodiment, the methods and compositions according to the subject invention lead to an increase in SOC in an area of soil, by at least 1%, 5%, 10%, 20%, 30%, 40%, 50%, 60%, 70%, 80%, 90%, 100%, 150%, 200%, or more, compared to similar untreated areas.

In one embodiment, the methods and compositions according to the subject invention lead to an increase in soil water retention by at least 1%, 5%, 10%, 20%, 30%, 40%, 50%, 60%, 70%, 80%, 90%, 100%, 150%, 200%, or more, compared to similar untreated areas.

In one embodiment, the methods and compositions according to the subject invention lead to a decrease in water usage by at least 1%, 5%, 10%, 20%, 30%, 40%, 50%, 60%, 70%, 80%, 90%, 100%, 150%, 200%, or more, compared to similar untreated areas.

In one embodiment, the methods and compositions according to the subject invention lead to decrease in soil-borne emissions of GHG, such as CO2, N2O and/or CH4, by at least 1%, 5%, 10%, 20%, 30%, 40%, 50%, 60%, 70%, 80%, 90%, 100%, or more, compared to similar untreated soil.

Microbial Soil Treatment Compositions

In certain embodiments, the subject invention provides microbial soil treatment compositions comprising one or more soil-colonizing microorganisms and/or growth by-products thereof, such as biosurfactants, enzymes, polysaccharides and/or other metabolites. The composition may also comprise the fermentation broth/medium in which the microorganism(s) were produced.

In some embodiments, the microorganisms of the subject invention have a CUE greater than microbes already present in the soil to which they are applied. In some embodiments, the microorganisms of the subject composition are "high CUE," meaning the percentage of carbon they allocate to biomass production is greater than the percentage allocated to respiration.

In certain embodiments, the microorganisms are bacteria, yeasts and/or fungi. In some embodiments, the composition comprises more than one type and/or species of microorganism. Advantageously, in some embodiments, the microorganisms colonize the rhizosphere and convert root exudates and digested organic matter into bulky, carbon-rich microbial biomass and necromass (dead cells).

In preferred embodiments, the microbe-based compositions according to the subject invention are non-toxic and can be applied in high concentrations without causing irritation to, for example, the skin or digestive tract of a human or other non-pest animal. Thus, the subject invention is particularly useful where application of the microbe-based compositions occurs in the presence of living organisms, such as growers and livestock.

In one embodiment, multiple microorganisms can be used together, where the microorganisms create a synergistic benefit towards plant and root health, as well as increasing SOC, preventing soil degradation and/or rebuilding degraded soils.

The species and ratio of microorganisms and other ingredients in the composition can be customized and optimized for specific local conditions at the time of application, such as, for example, which soil type, plant and/or crop is being treated; what season, climate and/or time of year it is when a composition is being applied; and what mode and/or rate of application is being utilized. Thus, the composition can be customizable for any given site.

The microorganisms in the plant health-promoting composition may be in an active or inactive form, or in the form of vegetative cells, spores and/or any other form of propagule.

The microorganisms useful according to the subject invention can be, for example, non-plant-pathogenic strains of bacteria, yeast and/or fungi. These microorganisms may be natural, or genetically modified microorganisms. For example, the microorganisms may be transformed with specific genes to exhibit specific characteristics. The microorganisms may also be mutants of a desired strain. As used herein, "mutant" means a strain, genetic variant or subtype of a reference microorganism, wherein the mutant has one or more genetic variations (e.g., a point mutation, missense mutation, nonsense mutation, deletion, duplication, frameshift mutation or repeat expansion) as compared to the reference microorganism. Procedures for making mutants are well known in the microbiological art. For example, UV mutagenesis and nitrosoguanidine are used extensively toward this end.

In certain embodiments, the microorganisms are yeasts or fungi. Yeast and fungus species suitable for use according to the current invention, include *Aureobasidium* (e.g., *A. pullulans*), *Blakeslea, Candida* (e.g., *C. apicola, C. bombicola, C. nodaensis*), *Cryptococcus, Debaryomyces* (e.g., *D. hansenii*), *Entomophthora, Hanseniaspora*, (e.g., *H. uvarum*), *Hansenula, Issatchenkia, Kluyveromyces* (e.g., *K. phaffii*), *Meyerozyma* (e.g., *M. guilliermondii, M. caribbica*, MEC14XN) *Mortierella, Mycorrhiza, Penicillium, Phycomyces, Pichia* (e.g., *P. anomala, P. guilliermondii, P. occidentalis, P. kudriavzevii*), *Pleurotus* spp. (e.g., *P. ostreatus*), *Pseudozyma* (e.g., *P. aphidis*), *Saccharomyces* (e.g., *S. boulardii* sequela, *S. cerevisiae, S. torula*), *Starmerella* (e.g., *S. bombicola*), *Torulopsis, Trichoderma* (e.g., *T. reesei, T. harzianum, T. hamatum, T. viride*), *Ustilago* (e.g., *U. maydis*), *Wickerhamomyces* (e.g., *W. anomalus*), *Williopsis* (e.g., *W. mrakii*), *Zygosaccharomyces* (e.g., *Z. bailii*), and mycorrhizal fungi.

As used herein, "mycorrhizal fungi" includes any species of fungus that forms a non-parasitic mycorrhizal relationship with a plant's roots. The fungi can be ectomycorrhizal fungi and/or endomycorrhizal fungi, including subtypes thereof (e.g., arbuscular, ericoid, and orchid mycorrhizae).

Non-limiting examples of mycorrhizal fungi according to the subject invention include species belong to Glomeromycota, Basidiomycota, Ascomycota, Zygomycota, Helotiales, and Hymenochaetales, as well as *Acaulospora* spp. (e.g., *A. alpina, A. brasiliensis, A. foveata*), *Amanita* spp. (e.g., *A. muscaria, A. phalloides*), *Amphinema* spp. (e.g., *A. byssoides, A. diadema, A. rugosum*), *Astraeus* spp. (e.g., *A. hygrometricum*), *Byssocorticium* spp. (e.g., *B. atrovirens*), *Byssoporia terrestris* (e.g., *B. terrestris sartoryi, B. terrestris lilacinorosea, B. terrestris aurantiaca, B. terrestris sublutea, B. terrestris parksii*), *Cairneyella* spp. (e.g., *C. variabilis*), *Cantherellus* spp. (e.g., *C. cibarius, C. minor, C. cinnabarinus, C. friesii*), *Cenococcum* spp. (e.g., *C. geophilum*), *Ceratobasidium* spp. (e.g., *C. cornigerum*), *Cortinarius* spp. (e.g., *C. austrovenetus, C. caperatus, C. violaceus*), *Endogone* spp. (e.g., *E. pisiformis*), *Entrophospora* spp. (e.g., *E. colombiana*), *Funneliformis* spp. (e.g., *F. mosseae*), *Gamarada* spp. (e.g., *G. debralockiae*), *Gigaspora* spp. (e.g., *G. gigantean, G. margarita*), *Glomus* spp. (e.g., *G. aggregatum, G. brasilianum, G. clarum, G. deserticola, G. etunicatum, G. fasciculatum G. intraradices, G. lamellosum, G. macrocarpum, G. monosporum, G. mosseae, G. versiforme*), *Gomphidius* spp. (e.g., *G. glutinosus*), *Hebeloma* spp. (e.g., *H. cylindrosporum*), *Hydnum* spp. (e.g., *H. repandum*), *Hymenoscyphus* spp. (e.g., *H. ericae*), *Inocybe* spp. (e.g., *I. bongardii, I. sindonia*), *Lactarius* spp. (e.g., *L. hygrophoroides*), *Lindtneria* spp. (e.g., *L. brevispora*), *Melanogaster* spp. (e.g., *M. ambiguous*), *Meliniomyces* spp. (e.g., *M. variabilis*), *Morchella* spp., *Mortierella* spp. (e.g., *M. polycephala*), *Oidiodendron* spp. (e.g., *O. maius*), *Paraglomus* spp. (e.g., *P. brasilianum*), *Paxillus* spp. (e.g., *P. involutus*), *Penicillium* spp. (e.g., *P. pinophilum, P. thomili*), *Peziza* spp. (e.g., *P. whitei*), *Pezoloma* spp. (e.g., *P. ericae*); *Phlebopus* spp. (e.g., *P. marginatus*), *Piloderma* spp. (e.g., *P. croceum*), *Pisolithus* spp. (e.g., *P. tinctorius*), *Pseudotomen-*

*tella* spp. (e.g., *P. tristis*), *Rhizoctonia* spp., *Rhizodermea* spp. (e.g., *R. veluwensis*), *Rhizophagus* spp. (e.g., *R. irregularis*), *Rhizopogon* spp. (e.g., *R. luteorubescens, R. pseudoroseolus*), *Rhizoscyphus* spp. (e.g., *R. ericae*), *Russula* spp. (e.g., *R. livescens*), *Sclerocystis* spp. (e.g., *S. sinuosum*), *Scleroderma* spp. (e.g., *S. cepa, S. verrucosum*), *Scutellospora* spp. (e.g., *S. pellucida, S. heterogama*), *Sebacina* spp. (e.g., *S. sparassoidea*), *Setchelliogaster* spp. (e.g., *S. tenuipes*), *Suillus* spp. (e.g., *S. luteus*), *Thanatephorus* spp. (e.g., *T. cucumeris*), *Thelephora* spp. (e.g., *T. terrestris*), *Tomentella* spp. (e.g., *T. badia, T. cinereoumbrina, T. erinalis, T. galzinii*), *Tomentellopsis* spp. (e.g., *T. echinospora*), *Trechispora* spp. (e.g., *T. hymenocystis, T. stellulata, T. thelephora*), *Trichophaea* spp. (e.g., *T. abundans, T. woolhopeia*), *Tulasnella* spp. (e.g., *T. calospora*), and *Tylospora* spp. (e.g., T fibrillose).

In certain embodiments, the subject invention utilizes endomycorrhizal fungi, including fungi from the phylum Glomeromycota and the genera *Glomus, Gigaspora, Acaulospora, Sclerocystis*, and *Entrophospora*. Examples of endomycorrhizal fungi include, but not are not limited to, *Glomus aggregatum, Glomus brasilianum, Glomus clarum, Glomus deserticola, Glomus etunicatum, Glomus fasciculatum, Glomus intraradices* (*Rhizophagus irregularis*), *Glomus lamellosum, Glomus macrocarpum, Gigaspora margarita, Glomus monosporum, Glomus mosseae* (*Funnelifomis mosseae*), *Glomus versiforme, Scutellospora heterogama*, and *Sclerocystis* spp.

In certain embodiments, the microorganisms are bacteria, including Gram-positive and Gram-negative bacteria. The bacteria may be, for example *Agrobacterium* (e.g., *A. radiobacter*), *Azotobacter* (*A. vinelandii, A. chroococcum*), *Azospirillum* (e.g., *A. brasiliensis*), *Bacillus* (e.g., *B. amyloliquefaciens, B. circulans, B. firmus, B. laterosporus, B. licheniformis, B. megaterium, B. mucilaginosus, B. subtilis*), *Frateuria* (e.g., *F. aurantia*), *Microbacterium* (e.g., *M. laevaniformans*), myxobacteria (e.g., *Myxococcus xanthus, Stignatella aurantiaca, Sorangium cellulosum, Minicystis rosea*), *Pantoea* (e.g., *P. agglomerans*), *Pseudomonas* (e.g., *P. aeruginosa, P. chlororaphis* subsp. *aureofaciens* (*Kluyver*), *P. putida*), *Rhizobium* spp., *Rhodospirillum* (e.g., *R. rubrum*), *Sphingomonas* (e.g., *S. paucimobilis*), and/or *Thiobacillus thiooxidans* (*Acidothiobacillus thiooxidans*).

In certain embodiments, the microorganisms are capable of fixing and/or solubilizing nitrogen, potassium, phosphorous and/or other micronutrients in soil.

In one embodiment, the microorganism is a nitrogen-fixing microorganism, or a diazotroph, selected from species of, for example, *Azospirillum, Azotobacter, Chlorobiaceae, Cyanothece, Frankia, Klebsiella, rhizobia, Trichodesmium, Meyerozyma guilliermondii, Meyerozyma caribbica, Bacillus subtilis* "B4" NRRL B-68031, and *Bacillus amyloliquefaciens* NRRL B-67928. In a specific embodiment, the nitrogen-fixing bacterium is *Azotobacter vinelandii, M. guilliermondii*, MEC14XN, *B. subtilis* B4, or *B. amyloliquefaciens* NRRL B-67928. Advantageously, in some embodiments, the use of a nitrogen-fixing microbe can enhance nitrogen uptake in soil, reduce fertilizer requirements, and/or reduce nitrous oxide soil emissions.

In another embodiment, the microorganism is a potassium-mobilizing microorganism, or KMB, selected from, for example, *Wickerhamomyces anomalus, Bacillus mucilaginosus, Frateuria aurantia* or *Glomus mosseae*. In a specific embodiment, the potassium-mobilizing microorganism is *W. anomalus* NRRL Y-68030 or *F. aurantia*.

In certain embodiments, the microorganism is a phosphorous-mobilizing microorganism, for example, *Wickerhamomyces anomalus*. This microbe produces beneficial organic acids and biosurfactants to help with nutrient and water mobilization, solubilization and absorption in soil. In some embodiments, *W. anomalus* can solubilize potassium in soil. Additionally, *W. anomalus* produces the enzyme phytase, which mobilizes phosphates into usable forms of inorganic phosphorus. Furthermore, *W. anomalus* produces ethyl acetate, which can, in certain embodiments, break down biofilms such as those that are formed by many plant vascular bacterial pathogens. In one embodiment, *W. anomalus* strain NRRL Y-68030 is utilized.

In one embodiment, the composition can comprise one or more *Bacillus* spp. microbes. For example, in one embodiment, the composition comprises *B. subtilis* (e.g., strain NRRL B-68031 "B4") and *B. amyloliquefaciens* (e.g., strain NRRL B-67928 "B. amy").

In one embodiment, the composition can comprise a *Trichoderma* spp. fungus, e.g. *T. harzianum* T-22.

In certain embodiments, the composition comprises *Trichoderma harzianum* and *Bacillus amyloliquefaciens*. In a specific embodiment, the *Bacillus* is B. amy.

In one embodiment, the composition can comprise from 1 to 99% *Trichoderma* by volume and from 99 to 1% *Bacillus* by weight or by volume. In some embodiments, the ratio of *Trichoderma* to *Bacillus* is about 1:100 to about 100:1, about 1:50, to about 50:1, about 1:25 to about 25:1, about 1:10 to about 10:1, about 1:9 to about 9:1, about 1:8 to about 8:1, about 1:7 to about 7:1, about 1:6 to about 6:1, about 1:5 to about 5:1 or about 1:4 to about 4:1.

In one embodiment, the microorganisms of the subject composition comprise about 5 to 20% of the total composition, or about 8 to 15%, or about 10 to 12% by weight. In one embodiment, the composition comprises about $1\times10^6$ to $1\times10^{12}$, $1\times10^7$ to $1\times10^{11}$, $1\times10^8$ to $1\times10^{10}$, or $1\times10^9$ CFU/ml of *Trichoderma*. In one specific embodiment, the composition comprises about $1\times10^6$ to $1\times10^{12}$, $1\times10^7$ to $1\times10^{11}$, $1\times10^8$ to $1\times10^{10}$, or $1\times10^9$ CFU/ml of *Bacillus*.

Other exemplary microbes can include, for example, *Pseudomonas chlororaphis, Starmerella bombicola, Saccharomyces boulardii, Debaryomyces hansenii, Pichia occidentalis*, and/or *Pichia kudriavzevii*.

The species and ratio of microorganisms and other ingredients in the composition can be customized according to, for example, the plant being treated, the soil type where the plant is growing, the health of the plant at the time of treatment, the species of pest or pathogen affecting the plant, as well as other factors.

Advantageously, in some embodiments, the combination of microbes works synergistically with one another to promote plant health, growth and/or yields. In an exemplary embodiment, *Trichoderma harzianum* and B. amy work in synergy with one another as one composition, to promote plant health. *Trichoderma harzianum* is a beneficial fungus that attaches to, and elongates roots, which aids in the increase of nutrient uptake. B. amy is a beneficial rhizobacterium that produces organic acids that help to solubilize and move nutrients, such as NPK, in the soil, ultimately into the rootzone where the plant roots can absorb them. In some embodiments, B. amy is also useful for nitrogen fixation. Both of these microbes also produce biosurfactants, which improve water use efficiency and penetration and uptake of water and nutrients through the roots.

In one embodiment, the composition comprises *B. amyloliquefaciens* NRRL B-67928 "B. amy." A culture of the *B. amyloliquefaciens* "B. amy" microbe has been deposited with the Agricultural Research Service Northern Regional Research Laboratory (NRRL), 1400 Independence Ave., S.W., Washington, DC, 20250, USA. The deposit has been assigned accession number NRRL B-67928 by the depository and was deposited on Feb. 26, 2020.

In one embodiment, the composition comprises *B. subtilis* NRRL B-68031 "B4." A culture of the B4 microbe has been deposited with the Agricultural Research Service Northern Regional Research Laboratory (NRRL), 1400 Independence Ave., S.W., Washington, DC, 20250, USA. The deposit has been assigned accession number NRRL B-68031 by the depository and was deposited on May 6, 2021.

In one embodiment, the composition comprises *W. anomalus* NRRL Y-68030. A culture of this microbe has been deposited with the Agricultural Research Service Northern Regional Research Laboratory (NRRL), 1400 Independence Ave., S.W., Washington, DC, 20250, USA. The deposit has been assigned accession number NRRL Y-68030 by the depository and was deposited on May 6, 2021.

Each of the subject cultures has been deposited under conditions that assure that access to the culture will be available during the pendency of this patent application to one determined by the Commissioner of Patents and Trademarks to be entitled thereto under 37 CFR 1.14 and 35 U.S.C 122. The deposit is available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposit will be stored and made available to the public in accord with the provisions of the Budapest Treaty for the Deposit of Microorganisms, i.e., it will be stored with all the care necessary to keep it viable and uncontaminated for a period of at least five years after the most recent request for the furnishing of a sample of the deposit, and in any case, for a period of at least 30 (thirty) years after the date of deposit or for the enforceable life of any patent which may issue disclosing the culture. The depositor acknowledges the duty to replace the deposit should the depository be unable to furnish a sample when requested, due to the condition of the deposit. All restrictions on the availability to the public of the subject culture deposit will be irrevocably removed upon the granting of a patent disclosing it.

In a specific embodiment, the concentration of each microorganism included in the composition is $1\times10^6$ to $1\times10^{13}$ CFU/g, $1\times10^7$ to $1\times10^{12}$ CFU/g, $1\times10^8$ to $1\times10^{11}$ CFU/g, or $1\times10^9$ to $1\times10^{10}$ CFU/g of the composition.

In one embodiment, the total microbial cell concentration of the composition is at least $1\times10^6$ CFU/g, including up to $1\times10^9$ CFU/g, $1\times10^{10}$, $\mathbf{1\times10^{11}}$, $\mathbf{1\times10^{12}}$ and/or $1\times10^{13}$ or more CFU/g. In one embodiment, the microorganisms of the subject composition comprise about 5 to 20% of the total composition by volume or by weight, or about 8 to 15%, or about 10 to 12%.

The composition can comprise the leftover fermentation substrate and/or purified or unpurified growth by-products, such as enzymes, biosurfactants and/or other metabolites. The microbes can be live or inactive.

The microbes and microbe-based compositions of the subject invention have a number of beneficial properties that are useful for, e.g., increasing plant biomass and/or forming/stabilizing carbo-mineral soil aggregates. For example, the compositions can comprise products resulting from the growth of the microorganisms, such as biosurfactants, proteins and/or enzymes, either in purified or crude form. Furthermore, the microorganisms can enhance plant growth, induce auxin production, enable solubilization, absorption and/or balance of nutrients in the soil, and protect plants from pests and pathogens.

The composition can comprise the fermentation medium containing a live and/or an inactive culture, the purified or crude form growth by-products, such as biosurfactants, enzymes, and/or other metabolites, and/or any residual nutrients.

The product of fermentation may be used directly, with or without extraction or purification. If desired, extraction and purification can be easily achieved using standard extraction and/or purification methods or techniques described in the literature.

The microorganisms in the composition may be in an active or inactive form, or in the form of vegetative cells, reproductive spores, mycelia, hyphae, conidia or any other form of microbial propagule. The composition may also contain a combination of any of these microbial forms.

In one embodiment, when a combination of strains of microorganism are included in the composition, the different strains of microbe are grown separately and then mixed together to produce the composition.

Advantageously, in accordance with the subject invention, the composition may comprise the medium in which the microbes were grown. The composition may be, for example, at least, by weight, 1%, 5%, 10%, 25%, 50%, 75%, or 100% growth medium. The amount of biomass in the composition, by weight, may be, for example, anywhere from 0% to 100% inclusive of all percentages therebetween.

In one embodiment, the composition is preferably formulated for application to soil, seeds, whole plants, or plant parts (including, but not limited to, roots, tubers, stems, flowers and leaves). In certain embodiments, the composition is formulated as, for example, liquid, dust, granules, microgranules, pellets, wettable powder, flowable powder, emulsions, microcapsules, oils, or aerosols.

To improve or stabilize the effects of the composition, it can be blended with suitable adjuvants and then used as such or after dilution, if necessary. In preferred embodiments, the composition is formulated as a liquid, a concentrated liquid, or as dry powder or granules that can be mixed with water and other components to form a liquid product. In one embodiment, the composition can comprise glucose (e.g., in the form of molasses), in addition to an osmoticum substance, to ensure optimum osmotic pressure during storage and transport of the dry product.

Further components can be added to the composition, for example, buffering agents, carriers, other microbe-based compositions produced at the same or different facility, viscosity modifiers, preservatives, nutrients for microbe growth, tracking agents, biocides, other microbes, surfactants, emulsifying agents, lubricants, solubility controlling agents, pH adjusting agents, preservatives, stabilizers and ultra-violet light resistant agents.

The pH of the composition should be suitable for the microorganism of interest as well as for the soil environment to which it will be applied. In some embodiments, the pH is about 2.0 to about 10.0, about 2.0 to about 9.5, about 2.0 to about 9.0, about 2.0 to about 8.5, about 2.0 to about 8.0, about 2.0 to about 7.5, about 2.0 to about 7.0, about 3.0 to about 7.5, about 4.0 to about 7.5, about 5.0 to about 7.5, about 5.5 to about 7.0, about 6.5 to about 7.5, about 3.0 to about 5.5, about 3.25 to about 4.0, or about 3.5. Buffers, and pH regulators, such as carbonates and phosphates, may be used to stabilize pH near a preferred value.

Optionally, the composition can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C.

The microbe-based compositions may be used without further stabilization, preservation, and storage, however. Advantageously, direct usage of these microbe-based compositions preserves a high viability of the microorganisms, reduces the possibility of contamination from foreign agents and undesirable microorganisms, and maintains the activity of the by-products of microbial growth.

In other embodiments, the composition (microbes, growth medium, or microbes and medium) can be placed in containers of appropriate size, taking into consideration, for example, the intended use, the contemplated method of application, the size of the fermentation vessel, and any mode of transportation from microbe growth facility to the location of use. Thus, the containers into which the microbe-based composition is placed may be, for example, from 1 pint to 1,000 gallons or more. In certain embodiments the containers are 1 gallon, 2 gallons, 5 gallons, 25 gallons, or larger.

The compositions can be used in combination with other agricultural compounds and/or crop management systems. In one embodiment, the composition can optionally comprise, or be applied with, for example, natural and/or chemical pesticides, repellants, herbicides, fertilizers, water treatments, non-ionic surfactants and/or soil amendments. Preferably, however, the composition does not comprise and/or is not used with benomyl, dodecyl dimethyl ammonium chloride, hydrogen dioxide/peroxyacetic acid, imazilil, propiconazole, tebuconazole, or triflumizole.

If the composition is mixed with compatible chemical additives, the chemicals are preferably diluted with water prior to addition of the subject composition.

In one embodiment, the subject compositions are compatible for use with agricultural compounds characterized as antiscalants, such as, e.g., hydroxyethylidene diphosphonic acid;

bactericides, such as, e.g., streptomycin sulfate and/or Galltrol® (*A. radiobacter* strain K84);

biocides, such as, e.g., chlorine dioxide, didecyldimethyl ammonium chloride, halogenated heterocyclic, and/or hydrogen dioxide/peroxyacetic acid;

fertilizers, such as, e.g., N—P—K fertilizers, calcium ammonium nitrate 17-0-0, potassium thiosulfate, nitrogen (e.g., 10-34-0, Kugler KQ-XRN, Kugler KS-178C, Kugler KS-2075, Kugler LS 6-24-6S, UN 28, UN 32), and/or potassium;

fungicides, such as, e.g., chlorothalonil, manicozeb hexamethylenetetramine, aluminum tris, azoxystrobin, *Bacillus* spp. (e.g., *B. licheniformis* strain 3086, *B. subtilis, B. subtilis* strain QST 713), benomyl, boscalid, pyraclostrobin, captan, carboxin, chloroneb, chlorothalonil, copper culfate, cyazofamid, dicloran, dimethomorph, etridiazole, thiophanate-methyl, fenamidone, fenarimol, fludioxonil, fluopicolide, flutolanil, iprodione, mancozeb, maneb, mefanoxam, fludioxonil, mefenoxam, metalaxyl, myclobutanil, oxathiapiprolin, pentachloronitrobenzene (quintozene), phosphorus acid, propamocarb, propanil, pyraclostrobin, *Reynoutria sachalinensis, Streptomyces* spp. (e.g., *S. griseoviridis* strain K61, *S. lydicus* WYEC 108), sulfur, urea, thiabendazole, thiophanate methyl, thiram, triadimefon, triadimenol, and/or vinclozolin;

growth regulators, such as, e.g., ancymidol, chlormequat chloride, diaminozide, paclobutrazol, and/or uniconazole;

herbicides, such as, e.g., glyphosate, oxyfluorfen, and/or pendimethalin;

insecticides, such as, e.g., acephate, azadirachtin, *B. thuringiensis* (e.g., subsp. *israelensis* strain AM 65-52), *Beauveria bassiana* (e.g., strain GHA), carbaryl, chlorpyrifos, cyantraniliprole, cyromazine, dicofol, diazinon, dinotefuran, imidacloprid, *Isaria fumosorosae* (e.g., Apopka strain 97), lindane, and/or malathion;

water treatments, such as, e.g., hydrogen peroxide (30-35%), phosphonic acid (5-20%), and/or sodium chlorite;

as well as glycolipids, lipopeptides, deet, diatomaceous earth, citronella, essential oils, mineral oils, garlic extract, chili extract, and/or any known commercial and/or homemade pesticide that is determined to be compatible by the skilled artisan having the benefit of the subject disclosure.

Preferably, the composition does not comprise and/or is not applied simultaneously with, or within 7 to 10 days before or after, application of the following compounds: benomyl, dodecyl dimethyl ammonium chloride, hydrogen dioxide/peroxyacetic acid, imazilil, propiconazole, tebuconazole, or triflumizole.

In certain embodiments, the compositions and methods can be used to enhance the effectiveness of other compounds, for example, by enhancing the penetration of a pesticidal compound into a plant or pest, or enhancing the bioavailability of a nutrient to plant roots. The microbe-based products can also be used to supplement other treatments, for example, antibiotic treatments. Advantageously, the subject invention helps reduce the amount of antibiotics that must be administered to a crop or plant in order to be effective at treating and/or preventing bacterial infection.

Growth of Microbes According to the Subject Invention

The subject invention utilizes methods for cultivation of microorganisms and production of microbial metabolites and/or other by-products of microbial growth. The subject invention further utilizes cultivation processes that are suitable for cultivation of microorganisms and production of microbial metabolites on a desired scale. These cultivation processes include, but are not limited to, submerged cultivation/fermentation, solid state fermentation (SSF), and modifications, hybrids and/or combinations thereof.

As used herein "fermentation" refers to cultivation or growth of cells under controlled conditions. The growth could be aerobic or anaerobic. In preferred embodiments, the microorganisms are grown using SSF and/or modified versions thereof.

In one embodiment, the subject invention provides materials and methods for the production of biomass (e.g., viable cellular material), extracellular metabolites (e.g. small molecules and proteins), residual nutrients and/or intracellular components (e.g. enzymes and other proteins).

The microbe growth vessel used according to the subject invention can be any fermenter or cultivation reactor for industrial use. hi one embodiment, the vessel may have functional controls/sensors or may be connected to functional controls/sensors to measure important factors in the cultivation process, such as pH, oxygen, pressure, temperature, humidity, microbial density and/or metabolite concentration.

In a further embodiment, the vessel may also be able to monitor the growth of microorganisms inside the vessel (e.g., measurement of cell number and growth phases).

Alternatively, a daily sample may be taken from the vessel and subjected to enumeration by techniques known in the art, such as dilution plating technique. Dilution plating is a simple technique used to estimate the number of organisms in a sample. The technique can also provide an index by which different environments or treatments can be compared.

In one embodiment, the method includes supplementing the cultivation with a nitrogen source. The nitrogen source can be, for example, potassium nitrate, ammonium nitrate ammonium sulfate, ammonium phosphate, ammonia, urea, and/or ammonium chloride. These nitrogen sources may be used independently or in a combination of two or more.

The method can provide oxygenation to the growing culture. One embodiment utilizes slow motion of air to remove low-oxygen containing air and introduce oxygenated air. In the case of submerged fermentation, the oxygenated air may be ambient air supplemented daily through mechanisms including impellers for mechanical agitation of liquid, and air spargers for supplying bubbles of gas to liquid for dissolution of oxygen into the liquid.

The method can further comprise supplementing the cultivation with a carbon source. The carbon source can be a carbohydrate, such as glucose, sucrose, lactose, fructose, trehalose, mannose, mannitol, and/or maltose; organic acids such as acetic acid, fumaric acid, citric acid, propionic acid, malic acid, malonic acid, and/or pyruvic acid; alcohols such as ethanol, propanol, butanol, pentanol, hexanol, isobutanol, and/or glycerol; fats and oils such as soybean oil, canola oil, rice bran oil, olive oil, corn oil, sunflower oil, sesame oil, and/or linseed oil; etc. These carbon sources may be used independently or in a combination of two or more.

In one embodiment, growth factors and trace nutrients for microorganisms are included in the medium. This is particularly preferred when growing microbes that are incapable of producing all of the vitamins they require. Inorganic nutrients, including trace elements such as iron, zinc, copper, manganese, molybdenum and/or cobalt may also be included in the medium. Furthermore, sources of vitamins, essential amino acids, and microelements can be included, for example, in the form of flours or meals, such as corn flour, or in the form of extracts, such as yeast extract, potato extract, beef extract, soybean extract, banana peel extract, and the like, or in purified forms. Amino acids such as, for example, those useful for biosynthesis of proteins, can also be included.

In one embodiment, inorganic salts may also be included. Usable inorganic salts can be potassium dihydrogen phosphate, dipotassium hydrogen phosphate, disodium hydrogen phosphate, magnesium sulfate, magnesium chloride, iron sulfate, iron chloride, manganese sulfate, manganese chloride, zinc sulfate, lead chloride, copper sulfate, calcium chloride, sodium chloride, calcium carbonate, and/or sodium carbonate. These inorganic salts may be used independently or in a combination of two or more.

In some embodiments, the method for cultivation may further comprise adding additional acids and/or antimicrobials in the medium before, and/or during the cultivation process. Antimicrobial agents or antibiotics are used for protecting the culture against contamination.

Additionally, antifoaming agents may also be added to prevent the formation and/or accumulation of foam during submerged cultivation.

The pH of the mixture should be suitable for the microorganism of interest. Buffers, and pH regulators, such as carbonates and phosphates, may be used to stabilize pH near a preferred value. When metal ions are present in high concentrations, use of a chelating agent in the medium may be necessary.

The microbes can be grown in planktonic form or as biofilm. In the case of biofilm, the vessel may have within it a substrate upon which the microbes can be grown in a biofilm state. The system may also have, for example, the capacity to apply stimuli (such as shear stress) that encourages and/or improves the biofilm growth characteristics.

The pH of the culture should be suitable for the microorganism of interest as well as for the soil environment to which the composition will be applied. In some embodiments, the pH is about 2.0 to about 10.0, about 2.0 to about 9.5, about 2.0 to about 9.0, about 2.0 to about 8.5, about 2.0 to about 8.0, about 2.0 to about 7.5, about 2.0 to about 7.0, about 3.0 to about 7.5, about 4.0 to about 7.5, about 5.0 to about 7.5, about 5.5 to about 7.0, about 6.5 to about 7.5, about 3.0 to about 5.5, about 3.25 to about 4.0, or about 3.5. Buffers, and pH regulators, such as carbonates and phosphates, may be used to stabilize pH near a preferred value.

In one embodiment, the method of cultivation is carried out at about 5° to about 100° C., about 15° to about 60° C., about 20° to about 50° C., about 20° to about 45° C., about 25° to about 40° C., about 25° to about 37° C., about 25° to about 35° C., about 30° to about 35° C., about 24° to about 28° C., or about 22° to about 25° C. In one embodiment, the cultivation may be carried out continuously at a constant temperature. In another embodiment, the cultivation may be subject to changing temperatures.

In one embodiment, the equipment used in the method and cultivation process is sterile. The cultivation equipment such as the reactor/vessel may be separated from, but connected to, a sterilizing unit, e.g., an autoclave. The cultivation equipment may also have a sterilizing unit that sterilizes in situ before starting the inoculation. Air can be sterilized by methods know in the art. For example, the ambient air can pass through at least one filter before being introduced into the vessel. In other embodiments, the medium may be pasteurized or, optionally, no heat at all added, where the use of low water activity and low pH may be exploited to control undesirable bacterial growth.

In one embodiment, the subject invention further provides a method for producing microbial metabolites such as, for example, biosurfactants, enzymes, proteins, ethanol, lactic acid, beta-glucan, peptides, metabolic intermediates, polyunsaturated fatty acid, and lipids, by cultivating a microbe strain of the subject invention under conditions appropriate for growth and metabolite production; and, optionally, purifying the metabolite. The metabolite content produced by the method can be, for example, at least 20%, 30%, 40%, 50%, 60%, 70%, 80%, or 90%.

The microbial growth by-product produced by microorganisms of interest may be retained in the microorganisms or secreted into the growth medium. The medium may contain compounds that stabilize the activity of microbial growth by-product.

The biomass content of the fermentation medium may be, for example, from 5 g/l to 180 g/l or more, or from 10 g/l to 150 g/l.

The cell concentration may be, for example, at least $1\times10^6$ to $1\times10^{13}$, $1\times10^7$ to $1\times10^{12}$, $1\times10^8$ to $1\times10^{11}$, or $1\times10^9$ to $1\times10^{10}$ CFU/ml.

The method and equipment for cultivation of microorganisms and production of the microbial by-products can be performed in a batch, a quasi-continuous process, or a continuous process.

In one embodiment, all of the microbial cultivation composition is removed upon the completion of the cultivation (e.g., upon, for example, achieving a desired cell density, or density of a specified metabolite). In this batch procedure, an entirely new batch is initiated upon harvesting of the first batch.

In another embodiment, only a portion of the fermentation product is removed at any one time. In this embodiment, biomass with viable cells, spores, conidia, hyphae and/or mycelia remains in the vessel as an inoculant for a new cultivation batch. The composition that is removed can be a cell-free medium or contain cells, spores, or other reproductive propagules, and/or a combination of thereof. In this manner, a quasi-continuous system is created.

Advantageously, the method does not require complicated equipment or high energy consumption. The microorganisms of interest can be cultivated at small or large scale on site and utilized, even being still-mixed with their media.

Advantageously, the microbe-based products can be produced in remote locations. The microbe growth facilities may operate off the grid by utilizing, for example, solar, wind and/or hydroelectric power.

Preparation of Microbe-Based Products

One microbe-based product of the subject invention is simply the fermentation medium containing the microorganisms and/or the microbial metabolites produced by the microorganisms and/or any residual nutrients. The product of fermentation may be used directly without extraction or purification. If desired, extraction and purification can be easily achieved using standard extraction and/or purification methods or techniques described in the literature.

The microorganisms in the microbe-based products may be in an active or inactive form, or in the form of vegetative cells, reproductive spores, conidia, mycelia, hyphae, or any other form of microbial propagule. The microbe-based products may also contain a combination of any of these forms of a microorganism.

In one embodiment, different strains of microbe are grown separately and then mixed together to produce the microbe-based product. The microbes can, optionally, be blended with the medium in which they are grown and dried prior to mixing.

In one embodiment, the different strains are not mixed together, but are applied to a plant and/or its environment as separate microbe-based products.

The microbe-based products may be used without further stabilization, preservation, and storage. Advantageously, direct usage of these microbe-based products preserves a high viability of the microorganisms, reduces the possibility of contamination from foreign agents and undesirable microorganisms, and maintains the activity of the by-products of microbial growth.

Upon harvesting the microbe-based composition from the growth vessels, further components can be added as the harvested product is placed into containers or otherwise transported for use. The additives can be, for example, buffers, carriers, other microbe-based compositions produced at the same or different facility, viscosity modifiers, preservatives, nutrients for microbe growth, surfactants, emulsifying agents, lubricants, solubility controlling agents, tracking agents, solvents, biocides, antibiotics, pH adjusting agents, chelators, stabilizers, ultra-violet light resistant agents, other microbes and other suitable additives that are customarily used for such preparations.

In one embodiment, buffering agents including organic and amino acids or their salts, can be added. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

In a further embodiment, pH adjusting agents include potassium hydroxide, ammonium hydroxide, potassium carbonate or bicarbonate, hydrochloric acid, nitric acid, sulfuric acid or a mixture.

In one embodiment, additional components such as an aqueous preparation of a salt, such as sodium bicarbonate or carbonate, sodium sulfate, sodium phosphate, sodium biphosphate, can be included in the formulation.

In certain embodiments, an adherent substance can be added to the composition to prolong the adherence of the product to plant parts. Polymers, such as charged polymers, or polysaccharide-based substances can be used, for example, xanthan gum, guar gum, levan, xylinan, gellan gum, curdlan, pullulan, dextran and others.

In preferred embodiments, commercial grade xanthan gum is used as the adherent. The concentration of the gum should be selected based on the content of the gum in the commercial product. If the xanthan gum is highly pure, then 0.001% (w/v—xanthan gum/solution) is sufficient.

In one embodiment, glucose, glycerol and/or glycerin can be added to the microbe-based product to serve as, for example, an osmoticum during storage and transport. In one embodiment, molasses can be included.

In one embodiment, prebiotics can be added to and/or applied concurrently with the microbe-based product to enhance microbial growth. Suitable prebiotics, include, for example, kelp extract, fulvic acid, chitin, humate and/or humic acid. In a specific embodiment, the amount of prebiotics applied is about 0.1 L/acre to about 0.5 L/acre, or about 0.2 L/acre to about 0.4 L/acre.

In one embodiment, specific nutrients are added to and/or applied concurrently with the microbe-based product to enhance microbial inoculation and growth. These can include, for example, soluble potash ($K_2O$), magnesium, sulfur, boron, iron, manganese, and/or zinc. The nutrients can be derived from, for example, potassium hydroxide, magnesium sulfate, boric acid, ferrous sulfate, manganese sulfate, and/or zinc sulfate.

Optionally, the product can be stored prior to use. The storage time is preferably short. Thus, the storage time may be less than 60 days, 45 days, 30 days, 20 days, 15 days, 10 days, 7 days, 5 days, 3 days, 2 days, 1 day, or 12 hours. In a preferred embodiment, if live cells are present in the product, the product is stored at a cool temperature such as, for example, less than 20° C., 15° C., 10° C., or 5° C.

In certain embodiments of the subject invention, a microbe growth facility produces fresh, high-density microorganisms and/or microbial growth by-products of interest on a desired scale. The microbe growth facility may be located at or near the site of application. The facility produces high-density microbe-based compositions in batch, quasi-continuous, or continuous cultivation.

The microbe growth facilities of the subject invention can be located at the location where the microbe-based product will be used (e.g., a citrus grove). For example, the microbe growth facility may be less than 300, 250, 200, 150, 100, 75, 50, 25, 15, 10, 5, 3, or 1 mile from the location of use.

Because the microbe-based product can be generated locally, without resort to the microorganism stabilization, preservation, storage and transportation processes of conventional microbial production, a much higher density of microorganisms can be generated, thereby requiring a smaller volume of the microbe-based product for use in the on-site application or which allows much higher density microbial applications where necessary to achieve the desired efficacy. This allows for a scaled-down bioreactor (e.g., smaller fermentation vessel, smaller supplies of starter material, nutrients and pH control agents), which makes the system efficient and can eliminate the need to stabilize cells or separate them from their culture medium. Local generation of the microbe-based product also facilitates the inclusion of the growth medium in the product. The medium can contain agents produced during the fermentation that are particularly well-suited for local use.

Locally-produced high density, robust cultures of microbes are more effective in the field than those that have remained in the supply chain for some time. The microbe-based products of the subject invention are particularly advantageous compared to traditional products wherein cells have been separated from metabolites and nutrients present in the fermentation growth media. Reduced transportation times allow for the production and delivery of fresh batches of microbes and/or their metabolites at the time and volume as required by local demand.

The microbe growth facilities of the subject invention produce fresh, microbe-based compositions, comprising the microbes themselves, microbial metabolites, and/or other components of the medium in which the microbes are grown. If desired, the compositions can have a high density of vegetative cells or propagules, or a mixture of vegetative cells and propagules.

In one embodiment, the microbe growth facility is located on, or near, a site where the microbe-based products will be used (e.g., a citrus grove), for example, within 300 miles, 200 miles, or even within 100 miles. Advantageously, this allows for the compositions to be tailored for use at a specified location. The formula and potency of microbe-based compositions can be customized for specific local conditions at the time of application, such as, for example, which soil type, plant and/or crop is being treated; what season, climate and/or time of year it is when a composition is being applied; and what mode and/or rate of application is being utilized.

Advantageously, distributed microbe growth facilities provide a solution to the current problem of relying on far-flung industrial-sized producers whose product quality suffers due to upstream processing delays, supply chain bottlenecks, improper storage, and other contingencies that inhibit the timely delivery and application of, for example, a viable, high cell-count product and the associated medium and metabolites in which the cells are originally grown.

Furthermore, by producing a composition locally, the formulation and potency can be adjusted in real time to a specific location and the conditions present at the time of application. This provides advantages over compositions that are pre-made in a central location and have, for example, set ratios and formulations that may not be optimal for a given location.

The microbe growth facilities provide manufacturing versatility by their ability to tailor the microbe-based products to improve synergies with destination geographies. Advantageously, in preferred embodiments, the systems of the subject invention harness the power of naturally-occurring local microorganisms and their metabolic by-products to improve GHG management.

The cultivation time for the individual vessels may be, for example, from 1 to 7 days or longer. The cultivation product can be harvested in any of a number of different ways.

Local production and delivery within, for example, 24 hours of fermentation results in pure, high cell density compositions and substantially lower shipping costs. Given the prospects for rapid advancement in the development of more effective and powerful microbial inoculants, consumers will benefit greatly from this ability to rapidly deliver microbe-based products.

EXAMPLES

A greater understanding of the present invention and of its many advantages may be had from the following examples, given by way of illustration. The following examples are illustrative of some of the methods, applications, embodiments and variants of the present invention. They are not to be considered as limiting the invention. Numerous changes and modifications can be made with respect to the invention.

Example 1—Compositions

Exemplified herein is a composition according to certain embodiments of subject invention for use in reducing GHGs, improving carbon utilization, and/or enhancing sequestration of carbon. This example is not to be intended as limiting. Formulations comprising other species of microorganisms, either in lieu of, or in addition to, those exemplified here, may be included in the composition.

The composition comprises a microbial inoculant comprising a *Trichoderma* spp. fungus and a *Bacillus* spp. bacterium. In specific instances, the composition comprises *Trichoderma harzianum* and *Bacillus amyloliquefaciens*. Even more specifically, the strain of *B. amyloliquefaciens* can be *B. amyloliquefaciens* NRRL B-67928.

In one embodiment, the composition can comprise from 1 to 99% *Trichoderma* by volume and from 99 to 1% *Bacillus* by volume. In some embodiments, the ratio of *Trichoderma* to *Bacillus* is about 1:100 to about 100:1, about 1:50, to about 50:1, about 1:25 to about 25:1, about 1:10 to about 10:1, about 1:9 to about 9:1, about 1:8 to about 8:1, about 1:7 to about 7:1, about 1:6 to about 6:1, about 1:5 to about 5:1 or about 1:4 to about 4:1.

In one embodiment, the microorganisms of the subject composition comprise about 5 to 20% of the total composition, or about 8 to 15%, or about 10 to 12% by weight. In one embodiment, the composition comprises about $1\times10^6$ to $1\times10^{12}$, $1\times10^7$ to $1\times10^{11}$, $1\times10^8$ to $1\times10^{10}$, or $1\times10^9$ CFU/ml of *Trichoderma*. In one specific embodiment, the composition comprises about $1\times10^6$ to $1\times10^{12}$, $1\times10^7$ to $1\times10^{11}$, $1\times10^8$ to $1\times10^{10}$, or $1\times10^9$ CFU/ml of *Bacillus*.

The composition can be mixed with and/or applied concurrently with additional "starter" materials to promote initial growth of the microorganisms in the composition. These can include, for example, prebiotics and/or nano-fertilizers (e.g., Aqua-Yield, NanoGro™)

One exemplary formulation of such growth-promoting "starter" materials comprises:

Soluble potash (K2O) (1.0% to 2.5%, or about 2.0%)
Magnesium (Mg) (0.25% to 0.75%, or about 0.5%)
Sulfur (S) (2.5% to 3.0%, or about 2.7%)
Boron (B) (0.01% to 0.05%, or about 0.02%)
Iron (Fe) (0.25% to 0.75%, or about 0.5%)
Manganese (Mn) (0.25% to 0.75%, or about 0.5%)
Zinc (Zn) (0.25% to 0.75%, or about 0.5%)
Humic acid (8% to 12%, or about 10%)

Kelp extract (5% to 10%, or about 6%)

Water (70% to 85%, or about 77% to 80%)

The microbial inoculant, and/or optional growth-promoting "starter" materials, are mixed with water in an irrigation system tank and applied to soil.

In specific instances, the composition comprises 10.0% by weight of the microbial inoculant, and 90% by weight water, where the inoculant comprises $1\times10^8$ CFU/mL *Trichoderma harzianum* and $1\times10^9$ CFU/mL of *Bacillus amyloliquefaciens*.

Example 2—Microbial Strains

The subject invention utilizes beneficial microbial strains. In certain embodiments, the microorganism is a strain of *Trichoderma*, such as, e.g., a strain of *T. harzianum, T. viride, T. longibrachia, T. asperellum, T. hamatum, T. koningii, T. reesei, T. guizhouse* and/or others.

Exemplary *Trichoderma harzianum* strains can include, but are not limited to, T-315 (ATCC 20671); T-35 (ATCC 20691); 1295-7 (ATCC 20846); 1295-22 [T-22] (ATCC 20847); 1295-74 (ATCC 20848); 1295-106 (ATCC 20873); T12 (ATCC 56678); WT-6 (ATCC 52443): Rifa T-77 (CMI CC 333646); T-95 (60850); T12m (ATCC 20737); SK-55 (No. 13327; BP 4326 NIBH (Japan)); RR17Bc (ATCC PTA 9708); TSHTH20-1 (ATCC PTA 10317); AB 63-3 (ATCC 18647); OMZ 779 (ATCC 201359); WC 47695 (ATCC 201575); m5 (ATCC 201645); (ATCC 204065); UPM-29 (ATCC 204075); T-39 (EPA 119200); and/or F11Bab (ATCC PTA 9709).

In some embodiments, the microbe is a *Bacillus* strain, such as, e.g., *B. subtilis, B. arnylolqieufaciens, B. licheniformis, B. megaterium, B. polymyxa* and/or others.

*B. subtilis* strains can include, e.g., *B. subtilis* B1 (ATCC PTA-123459) and/or B4 (NRRL B-68031).

*Bacillus amyloliquefaciens* strains can include, but are not limited to, NRRL B-67928, FZB24 (EPA 72098-5; BGSC 10A6), TA208, NJN-6, N2-4, N3-8, and those having ATCC accession numbers 23842, 23844, 23843, 23845, 23350 (strain DSM 7), 27505, 31592, 49763, 53495, 700385, BAA-390, PTA-7544, PTA-7545, PTA-7546, PTA-7549, PTA-7791, PTA-5819, PTA-7542, PTA-7790, and/or PTA-7541.

REFERENCES

Brummell, M. E., and S. D. Siciliano. (2011). "Measurement of Carbon Dioxide, Methane, Nitrous Oxide, and Water Potential in Soil Ecosystems." *Methods in Enzymology.* 496:115-137. Doi: 10.1016/B978-0-12-386489-5.00005-1. ("Brummell and Siciliano 2011").

Grandy, A. S. and G. P. Robertson (2007). "Land-Use Intensity Effects on Soil Organic Carbon Accumulation Rates and Mechanisms." *Ecosystems* 10:58-73. ("Grandy 2007").

Lal, R. (2018). "Digging deeper: A holistic perspective of factors affecting soil organic carbon sequestration in agroecosystems." *Glob. Change Biol.* 24:3285-3301. ("Lal 2018").

Panettieri, M. et al. (2013). "Moldboard plowing effects on soil aggregation and soil organic matter quality assessed by 13C CPMAS NMR and biochemical analyses." *Agric., Ecosys & Envt* 177:48-57. ("Panettieri 2013").

Possinger, A. R. et al. (2020). "Organo-organic and organo-mineral interfaces in soil at the nanometer scale." *Nature comm.* 11:6103. ("Possinger 2020").

Trivedi, P. et al. (2015). "Soil aggregate size mediates the impacts of cropping regimes on soil carbon and microbial communities." *Soil Biol & Biochem* 91:169-181. ("Trivedi 2015").

Trivedi, P. et al. (2017). "Soil aggregation and associated microbial communities modify the impact of agricultural management on carbon content." *Envtl Microbiol* 19(8), 3070-3086. ("Trivedi 2017").

We claim:

1. A method of irrigating soil and/or improving one or more properties of soil, which comprises applying an irrigation additive to soil, wherein said irrigation additive comprises a biosurfactant, and wherein said irrigation additive lowers the surface tension of an aqueous fluid applied to the soil, thereby improving dispersion, penetration and/or percolation of the aqueous fluid throughout the soil, and applying a microbial soil treatment composition to the soil about 30 days after application of the irrigation additive, wherein the microbial soil treatment composition comprises one or more beneficial microorganisms capable of colonizing soil and/or plant roots.

2. The method of claim 1, wherein the biosurfactant a microbial derived biosurfactant, or a surfactant derived from a naturally-occurring substrate, and wherein the surface active molecule has a micelle size less than 25 nm.

3. The method of claim 1, wherein the biosurfactant is selected from glycolipids, lipopeptides, flavolipids, phospholipids, fatty acid esters, lipoproteins, lipopolysaccharide-protein complexes, and polysaccharide-protein- fatty acid complexes.

4. The method of claim 1, wherein the biosurfactant is a sophorolipid.

5. The method of claim 1, wherein the irrigation additive is mixed with the aqueous liquid and applied to the soil via an irrigation system.

6. The method of claim 1, wherein the irrigation additive is applied to soil before or after the soil is irrigated with an aqueous liquid.

7. The method of claim 1, wherein the irrigation additive is applied at a concentration of 10 to 100 ppm with respect to the amount of aqueous fluid.

8. The method of claim 1, wherein the property of soil being improved is soil compaction, and wherein the irrigation additive improves compaction of the soil by increasing porosity of the soil.

9. The method of claim 1, wherein the irrigation additive is applied again about 30 days after application of the microbial soil treatment composition, followed by re-application of the microbial soil treatment composition after 30 more days, and wherein this is repeated until a desired level of irrigation and/or improvement in the one or more properties of soil is achieved.

10. The method of claim 1, wherein at least one of the one or more beneficial microorganisms is selected from *Trichoderma harzianum, Trichoderma viride, Trichoderma koningii, Trichoderma guizhouse, Bacillus amyloliquefaciens, Bacillus subtilis, Bacillus megaterium, Bacillus polymyxa, Bacillus licheniformis, Brevibacillus laterosporus, Meyerozyma guilliermondii, Pichia occidentalis, Pichia kudriavzevii, Wickerhamomyces anomalus*, and *Debaryomyces hansenii.*

11. The method of claim 1, comprising applying a beneficial microorganism selected from *Bacillus amyloliquefaciens* NRRL B-67928 and a *Trichoderma harzianum.*

12. The method of claim 1, comprising applying a beneficial microorganism that is *Wickerhamomyces anomalus* NRRL Y-68030.

13. The method of claim 1, comprising applying a beneficial microorganism that is *B. subtilis* B4 NRRL B-68031.

14. The method of claim 1, wherein water usage is reduced by at least 25% compared with soils irrigated without the irrigation additive.

* * * * *